(12) United States Patent
Millar et al.

(10) Patent No.: US 9,388,216 B2
(45) Date of Patent: Jul. 12, 2016

(54) METHODS OF TREATING REPRODUCTIVE CANCER

(75) Inventors: Robert Peter Millar, Edinburgh (GB); Stuart Russell Maudsley, Baltimore, MD (US); Rakel Lopez De Maturana Garmendia, Pamplona-Iruña (ES)

(73) Assignee: Medical Research Council, London (GB)

( * ) Notice: Subject to any disclaimer, the term of this patent is extended or adjusted under 35 U.S.C. 154(b) by 1395 days.

(21) Appl. No.: 12/308,482

(22) PCT Filed: May 1, 2007

(86) PCT No.: PCT/GB2007/001586
§ 371 (c)(1),
(2), (4) Date: Oct. 7, 2009

(87) PCT Pub. No.: WO2007/144554
PCT Pub. Date: Dec. 21, 2007

(65) Prior Publication Data
US 2010/0234303 A1   Sep. 16, 2010

Related U.S. Application Data

(60) Provisional application No. 60/805,042, filed on Jun. 16, 2006, provisional application No. 60/805,181, filed on Jun. 19, 2006.

(30) Foreign Application Priority Data

Aug. 12, 2006   (GB) .................................. 0616111.1

(51) Int. Cl.
| | |
|---|---|
| A61K 38/08 | (2006.01) |
| A61P 35/00 | (2006.01) |
| C07K 7/06 | (2006.01) |
| C12N 5/09 | (2010.01) |
| G01N 33/53 | (2006.01) |
| G01N 33/574 | (2006.01) |
| C07K 7/23 | (2006.01) |
| A61K 38/00 | (2006.01) |

(52) U.S. Cl.
CPC .. *C07K 7/23* (2013.01); *A61K 38/00* (2013.01)

(58) Field of Classification Search
None
See application file for complete search history.

(56) References Cited

U.S. PATENT DOCUMENTS 6,664,369 B1   12/2003   Lovas et al. ................... 530/328
2002/0052320 A1   5/2002   Trigg et al.

FOREIGN PATENT DOCUMENTS

| | | |
|---|---|---|
| GB | 2 237 571 A | 5/1991 |
| GB | 2 343 182 A | 5/2000 |
| GB | 2 344 287 | 6/2000 |
| WO | 01/28576 | 4/2001 |
| WO | 01/64236 | 9/2001 |
| WO | 01/74377 | 10/2001 |
| WO | 03/093304 | 11/2003 |
| WO | 2005/018657 | 3/2005 |

OTHER PUBLICATIONS

Jiang et al., "GnRH Antagonists: A New Generation of Long Acting Analogues Incorporating p-Ureido-phenylalanines at Positions 5 and 6", J. Med. Chem, 44:453-467 (2001).
Karten et al., "Gonadotropin-Releasing Hormone Analog Design. Structure-Function Studies Toward the Development of Agonists and Antagonists: Rationale and Perspective", Endocrine Reviews, 7(1):44-66 (2008).
Lopez de Maturana et al., "Gonadotropin-Releasing Hormone Analog Structural Determinants of Selectivity for Inhibition of Cell Growth: Support for the Concept of Ligand-Induced Selective Signaling", Molecular Endocrinology, 22(7):1711-1722 (2008).
Nakagawa et al., "Some Analogues of Luteinizing Hormone-Releasing Hormone with Substituents in Position 10", J. Med. Chem., 24:221-223 (1981).
Flanagan, Endocrinology, 139, 10, 1998.
Limonta, Frontiers in Neuroendocrinology, 24, 2003.
Blomenrohr et al., "Pivotal Role for the Cytoplasmic Carboxyl-Terminal Tail of a Nonmammalian Gonadotropin-Releasing Hormone Receptor in Cell Surface Expression, Ligand Binding, and Receptor Phosphorylation and Internalization," *Mol. Pharmacol.*, 56:1229-1237 (1999).
Chen et al., "Two Forms of Gonadotropin-releasing Hormone (GnRH) Are Expressed in Human Breast Tissue and Overexpressed in Breast Cancer: A Putative Mechanism for the Antiproliferative Effect of GnRH by Down-Regulation of Acidic ribosomal Phosphoproteins. P1 and P2," *Cancer Res.*, 62:1036-1044 (2002).
Chengalvala et al., "GnRH Agonists and Antagonists in Cancer Therapy," *Curr. Med. Chem.—Anti-Cancer Agents*, 3:399-410 (2003).
Chi et al., "Cloning and characterization of the human GnRH receptor," *Mol. Cell. Endocrinol.*, 91:R1-R6 (1993).
Davidson et al., "Gonadotropin-releasing Hormone-induced Activation of Diacylglycerol Kinase-ζ and Its Association with Active c-Src," *J. Biol. Chem.*, 279:11906-11916 (2004).
Davies et al., "Specificity and mechanism of action of some commonly used protein kinase inhibitors," *Biochem. J.*, 351:95-105 (2000).
Derossi et al., "Trojan peptides: the penetratin system for intracellular delivery," *Trends in Cell Biology*, 8:84-87 (1998).
Dikic et al., "Protein Tyrosine Kinase-Mediated Pathways in G Protein-Coupled Receptor Signaling," *Cell Biochem. Biophys.*, 30:369-387 (1999).
Emons et al., "GnRH antagonists in the treatment of gynecological and breast cancers," *Endocrine-Related Cancer*, 10:291-299 (2003).
Enomoto et al., "Human Type II GnRH Receptor Mediates Effects of GnRH on Cell Proliferation," *Zoolog. Sci.*, 21:763-770 (2004).

(Continued)

Primary Examiner — Susan Tran
Assistant Examiner — William Craigo
(74) Attorney, Agent, or Firm — Rodney J. Fuller; Booth Udall Fuller, PLC

(57) ABSTRACT

The present invention relates to agents, compositions and methods for use in medicine. In particular, the invention relates to agents related to GnRH peptides.

7 Claims, 25 Drawing Sheets

(56) References Cited

OTHER PUBLICATIONS

Figure 1A:
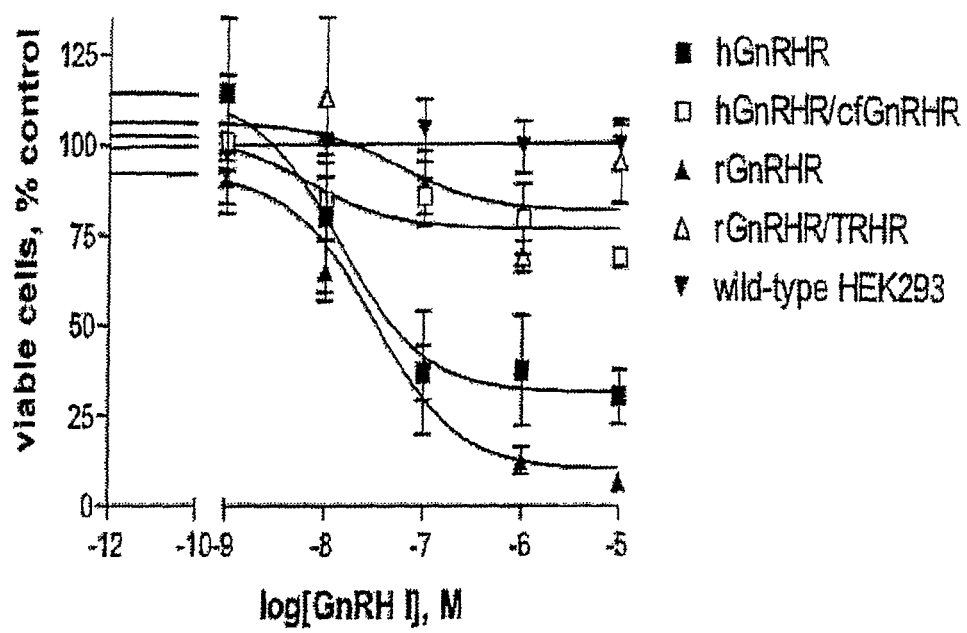

Farshori et al., "Activation and nuclear translocation of PKCδ, Pyk2 and ERK1/2 by gonadotropin releasing hormone in HEK293 cells," *J. Steroid Biochem. Mol. Biol.*, 85:337-347 (2003).
Flanagan et al., "Glutamate 301 of the Mouse Gonadotropin-releasing Hormone Receptor Confers Specificity for Arginine 8 of Mammalian Gonadotropin-releasing Hormone," *J. Biol. Chem.*, 269:22636-22641 (1994).
Folkers et al., "Decapeptides as effective agonists from L-amino acids biologically equivalent to the luteinizing hormone-releasing hormone," *Proc. Nat. Acad. Sci. USA*, 82:1070-1074 (1985).
Fromme et al., "Role of Aspartate7.32(302) of the Human Gonadotropin-Releasing Hormone Receptor in Stabilizing a High-Affinity Ligand Conformation," *Mol. Pharmacol.*, 60:1280-1287 (2001).
Fromme et al., "A Novel Retro-Inverso Gonadotropin-Releasing Hormone (GnRH) Immunogen Elicits Antibodies That Neutralize the Activity of Native GnRH," *Endocrinology*, 144:3262-3269 (2003).
Gnanapragasam et al. "Evidence that prostate gonadotropin-releasing hormone receptors mediate an anti-tumourigenic response to analogue therapy in hormone refractory prostate cancer," *J. Pathol.*, 206:205-213 (2005).
Grosse et al., "Epidermal Growth Factor Receptor Tyrosine Kinase Mediates Ras Activation by Gonadotropin-releasing Hormone," *J. Biol. Chem.*, 275:12251-12260 (2000).
Grundker et al., "Biology of the gonadotropin-releasing hormone system in gynecological cancers," *Eur. J. Endocrinol.*, 146:1-14 (2002).
Grundker et al., "Antiproliferative effects of the GnRH antagonist cetrorelix and of GnRH-II on human endometrial and ovarian cancer cells are not mediated through the GnRH type I receptor," *Eur. J. Endocrinol...*, 151:141-149 (2004).
Habibi et al., "Activity of vertebrate gonadotropin-releasing hormones and analogs with variant amino acid residues in positions 5, 7 and 8 in the goldfish pituitary," *Reg. Peptides*, 37:271-284 (1992).
Habibi et al., "Gonadotropin-Releasing Hormone: Structural and Functional Diversity," *Bioactive Peptides in Drug Discovery and Design*, 247-254 (1999).
Heding et al., "Gonadotropin-releasing Hormone Receptors with Intracellular Carboxyl-terminal Tails Undergo Acute Desensitization of Total Inositol Phosphate Production and Exhibit Accelerated Internalization Kinetics," *J. Biol. Chem.*, 273:11472-11477 (1998).
Heding et al., "The Rat Gonadotropin-Releasing Hormone Receptor Internalizes via a β-Arrestin-Independent, but Dynamin-Dependent, Pathway: Addition of a Carboxyl-Terminal Tail Confers β-Arrestin Dependency," *Endocrinology*, 141:299-306 (2000).
Hislop et al., "Differential Internalization of Mammalian and Nonmammalian Gonadotropin-releasing Hormone Receptors," *J. Biol. Chem.*, 276:39685-39694(2001).
Hislop et al., "Desensitization and Internalization of Human and *Xenopus* Gonadotropin-Releasing Hormone Receptors Expressed in αT4 Pituitary Cells Using Recombinant Adenovirus," *Endocrinology*, 141:4564-4575 (2000).
Kaiser et al., "Studies of Gonadotropin-Releasing Hormone (GnRH) Action Using GnRH Receptor-Expressing Pituitary Cell Lines," *Endocr. Rev.*, 18:46-70 (1997).
Kakar et al., "Cloning, Sequencing, and Expression of Human Gonadotropin Releasing Hormone (GnRH) Receptor," *Biochem. Biophys. Res. Comm.*, 189:289-295 (1992).
Kim et al., "Type II Gonadotropin-Releasing Hormone Stimulates p38 Mitogen-Activated Protein Kinase and Apoptosis in Ovarian Cancer Cells," *J. Clin. Endocrinol. Metab.*, 89(6):3020-3026 (2004).
Kimura et al., "Role of Mitogen-activated Protein Kinase/Extracellular Signal-regulated Kinase Cascade in Gonadotropin-releasing Hormone-induced Growth Inhibition of a Human Ovarian Cancer Cell Line," *Cancer Res.*, 59:5133-5142 (1999).

Kraus et al., "c-Src Is Activated by the Epidermal Growth Factor Receptor in a Pathway That Mediates JNK and ERK Activation by Gonadotropin-releasing Hormone in COS7 Cells," *J. Biol. Chem.*, 278:32618-32630 (2003).
Kraus et al., "Gonadotropin-Releasing Hormone Induces Apoptosis of Prostate Cancer Cells: Role of c-Jun $NH_2$-Terminal Kinase, Protein Kinase B, and Extracellular Signal-Regulated Kinase Pathways," *Cancer Res.*, 64:5736-5744 (2004).
Limonta et al., "The biology of gonadotropin hormone-releasing hormone: role in the control of tumor growth and progression in humans," *Front Neuroendocrinol.*, 24:279-295 (2003).
Lin et al., "Addition of Catfish Gonadotropin-Releasing Hormone (GnRH) Receptor Intracellular Carboxyl-Terminal Tail to Rat GnRH Receptor Alters Receptor Expression and Regulation," *Mol. Endocrinol.*, 12(3):161-171 (1998).
Lu et al., "Improved synthesis of 4-Alkoxybenzyl Alcohol Resin," J. Org. Chem., 46:3433-3436 (1981).
Luttrell, L.M., "G Protein-Coupled Receptor Signalling in Neuroendocrine Systems," *J. Mol. Endocrinol.*, 30:117-126 (2003).
Maiti et al., "GnRH-II Analogs for Selective Activation and Inhibition of Non-Mammalian and Type-II Mammalian GnRH Receptors," *Mol. Cells*, 16:173-179 (2003).
Maiti et al., "Differential Effects of Gonadotropin-Releasing Hormone (GnRH)-I and GnRH-II on Prostate Cancer Cell Signaling and Death," *J. Clin. Endocrinol. Metab.*, 90:4287-4298 (2005).
Maudsley et al., "Gonadotropin-Releasing Hormone (GnRH) Antagonists Promote Proapoptotic Signaling n Peripheral Reproductive Tumor Cells by Activating a $G\alpha_i$-Coupling State of the Type I GnRH Receptor," *Cancer Res.*, 64:7533-5444 (2004).
Mézière et al., "In Vivo T Helper Cell Response to Retro-Inverso Peptidomimetics," *J. Immunol.*, 159:3230-3237 (1997).
Miles et al., "Gonadotropin-Releasing Hormone Receptor-Mediated Growth Suppression of Immortalized LβT2 Gonadotrope and Stable HEK293 Cell Lines," *Endocrinology*, 145(1):194-204 (2004).
Millar et al., "Outside-In and Inside-Out Signaling: The New Concept that Selectivity of Ligand Binding at the Gonadotropin-Releasing Hormone Receptor Is Modulated by the Intracellular Environment," *Endocrinology*, 145(8):3590-3593 (2004).
Millar et al., "Chimeric Analogues of Vertebrate Gonadotropin-releasing Hormones Comprising Substitutions of the Variant Amino Acids in Positions 5, 7, and 8," *J. Biol. Chem.*, 264(35):21007-21013 (1989).
Millar et al., "Gonadotropin-Releasing Hormone Receptors," *Endocr. Rev.*, 25(2):235-275 (2004).
Momany, F.A., "Conformational Energy Analysis of the Molecule, Luteinizing Hormone-Releasing Hormone. 1. Native Decapeptide," *J. Am. Chem. Soc.*, 98(10):2990-2996 (1976).
Morgan et al., "A Transcriptionally Active Human Type II Gonadotropin-Releasing Hormone Receptor Gene Homolog Overlaps Two Genes in the Antisense Orientation on Chromosome 1Q.12," *Endocrinology*, 144(2):423-436 (2003).
Naor et al., "Mechanism of GnRH Receptor Signaling: Combinatorial Cross-Talk of $Ca^{2+}$ and Protein Kinase C," *Front Neuroendocrinol.*, 19:1-19 (1998).
Neill et al., "Newly recognized GnRH receptors: function and relative role," *TRENDS Endocrinol. Metab.*, 15(8):383-392 (2004).
Pawson et al., "Contrasting internalization kinetics of human and chicken Gonadotropin-Releasing Hormone Receptors mediated by C-terminal tail," *J Endocrinol.*, 156:R9-12 (1998).
Pfleger et al., "Conformational Constraint of Mammalian, Chicken, and Salmon GnRHs, But Not GnRH II, Enhances Binding at Mammalian and Nonmammalian Receptors: Evidence for Preconfiguration of GnRH II," *Mol. Endocrinol.*, 16(9):2155-2162 (2002).
Ratcliffe et al., "Bifunctional Gonadotropin-Releasing Hormone Antagonist-Progesterone Analogs with Increased Efficacy and Duration of Action," *Endocrinology*, 147(1):571-579 (2006).
Russell-Jones et al., "Synthesis of LHRH Antagonists Suitable for Oral Administration via the Vitamin $B_{12}$ Uptake System," *Bioconjug. Chem.*, 6:34-42 (1995).
Russell-Jones et al., "Vitamin $B_{12}$ Mediated Oral Delivery Systems for Granulocyte-Colony Stimulating Factor and Erythropoietin," *Bioconjug. Chem.*, 6:459-465 (1995).

(56) References Cited

OTHER PUBLICATIONS

Sealfon et al., "Molecular Mechanisms of Ligand Interaction with the Gonadotropin-Releasing Hormone Receptor," *Endocr Rev.*, 18(2):180-205 (1997).

Sherman et al., "Compatibility of Thioamides with Reverse Turn Features: Synthesis and Conformational Analysis of Two Model Cyclic Pseudopeptides Containing Thioamides as Backbone Modifications," *J. Am. Chem. Soc.*, 112:433-441 (1990).

Song et al., "Distinct roles of the ERK pathway in modulating apoptosis of Ras-transformed and non-transformed cells induced by anticancer agent FR901228," *FEBS Lett.*, 579:90-94 (2005).

Tanaka et al., "Protein Kinase C Promotes Apoptosis in LNCaP Prostate Cancer Cells through Activation of p38 MAPK and Inhibition of the Akt Survival Pathway," *J. Biol. Chem.*, 278(36):33753-33762 (2003).

Tsutsumi et al., "Cloning and Functional Expression of a Mouse Gonadotropin-Releasing Hormone Receptor," *Mol Endocrinol.*, 6:1163-1169 (1992).

Veber et al., "Conformationally restricted bicyclic analogs of somatostatin," *Proc. Natl. Acad. Sci.*, 75(6):2636-2640 (1978).

Vrecl et al., "Agonist-Induced Endocytosis and Recycling of the Gonadotropin-Releasing Hormone Receptor: Effect of β-Arrestin on Internalization Kinetics," *Mol. Endocrinol.*, 12(12):1818-1829 (1998).

Wang et al., "Preferential ligand selectivity of the monkey type-II gonadotropin-releasing hormone (GnRH) receptor for GnRH-2 and its analogs," *Mol. Cell. Endocrinol.*, 209:33-42 (2003).

Willars et al., "Lack of a C-terminal Tail in the Mammalian Gonadotropin-releasing Hormone Receptor Confers Resistance to Agonist-dependent Phosphorylation and Rapid Desensitization," *J. Biol. Chem.*, 274(42):30146-30153 (1999).

Millar, R., Goeffrey Harris Award Lecture presentation at the 6$^{th}$ International Congress of Neuroendocrinology, David L. Lawrence Convention Center, Pittsburgh, PA, Jun. 19, 2006.

Rich, D. H., "Inhibitors of cysteine proteinases," and "Inhibitors of aspartic proteinases," in: Dingle, J. T. et al., *Research monographs in cell and tissue physiology* (The Netherlands, Elsevier Science Publishers BV, 1986), Ch. 4, pp. 153-178 and Ch. 5, pp. 181-208.

Blomenrohr et al., "Chimaeric gonadotropin-releasing hormone (GnRH) peptides with improved affinity for the catfish (*Clarias gariepinus*) GnRH receptor", Biochem., J., 361:515-523 (2002).

FIG. 8C

|  | $IC_{50}$ | $EC_{50}$ (IP) | $EC_{50}$ (PA) |
|---|---|---|---|
| GnRH I | 6.68 ± 2.63 | 7.01 ± 1.66 | 94.97 ± 14.62 |
| GnRH II | 44.43 ± 12.43 * | 33.00 ± 11.07 * | 7.31 ± 5.55 ** |
| [His$^5$]GnRH I | 1.81 ± 1.17 | 1.92 ± 0.28 | 0.28 ± 0.08 *** |
| [Trp$^7$]GnRH I | 5.08 ± 0.53 | 8.38 ± 2.77 | 10.45 ± 3.99 ** |
| [Tyr$^8$]GnRH I | 182.2 ± 79.06 | 226.00 ± 81.02 *** | 22.46 ± 3.87 ** |
| [His$^5$,Trp$^7$]GnRH I | 12.14 ± 1.45 | 10.52 ± 2.92 | 8.37 ± 4.36 ** |
| [His$^5$,Tyr$^8$]GnRH I | 29.74 ± 8.70 | 51.95 ± 13.67 *** | 15.01 ± 2.90 ** |
| [Trp$^7$,Tyr$^8$]GnRH I | 113.7 ± 21.23 ** | 100.80 ± 42.66 * | 36.43 ± 7.24 * |

FIG. 8D

|  | $EC_{50}$ (IP) | $EC_{50}$ (PA) |
|---|---|---|
| GnRH I | 3.24 ± 0.94 | 327.00 ± 90.78 * |
| GnRH II | 20.07 ± 7.14 * | 49.09 ± 12.06 * |
| [His$^5$]GnRH I | 1.13 ± 0.55 | 6.22 ± 2.14 * |
| [Trp$^7$]GnRH I | 1.74 ± 0.62 | 16.91 ± 8.59 * |
| [Tyr$^8$]GnRH I | 76.80 ± 34.54 ** | 30.57 ± 2.91 * |
| [His$^5$,Trp$^7$]GnRH I | 8.11 ± 1.75 * | 16.55 ± 1.61 * |
| [His$^5$,Tyr$^8$]GnRH I | 30.06 ± 7.57 *** | 31.40 ± 2.81 * |
| [Trp$^7$,Tyr$^8$]GnRH I | 103.8 ± 49.73 * | 33.78 ± 12.96 * |

Activities of GnRH analogs relative to GnRH-II in Inhibition of cell number and inositol phosphate production in HEK 293 cells expressing the human GnRH receptor.

| | 1 | 2 | 3 | 4 | 5 | 6 | 7 | 8 | 9 | 10 | Activity (fold over GnRH-II) | |
|---|---|---|---|---|---|---|---|---|---|---|---|---|
| | | | | | | | | | | | Mean inhibition of cell numbers ± SEM | Mean Inositol Phosphate production |
| GnRH-II | pGlu | His | Trp | Ser | His | Gly | Trp | Tyr | Pro | Gly.NH₂ | 6.29+/-1.01 | 3.33 |
| pep 4 | | | | | | D-Arg | | | | | 1.18+/-0.36 | 1.20 |
| pep 6 | | | | | | D-Trp | | | | | 3.72+/-0.38 | 0.84 |
| pep 10 | | | | | Tyr | D-Lys | | Gln | | | 7.92+/-1.28 | 1.87 |
| pep 11 | | | | | Tyr | D-Lys | | Leu | | | 10.51+/-2.77 | 3.70 |
| pep 13 | | | | | Tyr | D-Lys | | | | | 29.8+/-7.9 | 3.70 |
| pep 15 | | | | | Tyr | D-Trp | | Arg | | | 51.13+/-12.1 | ND |
| pep 21 | | | | | | D-Lys | | | | | 2333.3+/-591.4 | ND |
| pep 23 | | | | | | D-Arg | | | | NHEt | 13.63+/-4.0 | 0.37 |
| pep 24 | | | | | | D-Arg | Leu | Arg | | | 4.8+/-1.37 | 0.15 |
| pep 26 | | | | | | D-Trp | | Arg | | | 38.5+/-6.7 | 11.93 |
| pep 27 | | | | | | D-Trp | Leu | Arg | | | 131+/-17.2 | 11.45 |
| pep 28 | | | | | | D-Tyr | Leu | Arg | | | 2.03+/-0.417 | 3.62 |
| pep 65 | | | | | | D-Ala | | | | | 1.1+/-1.04 | 0.52 |
| pep 66 | | | | | | D-Ser | | | | | | |
| pep 13-2 | | | | | Tyr | D-Lys | | Arg | | | 10.51+/-2.77 | 3.70 |

FIG. 15

SEQUENCE LISTING

```
<160> NUMBER OF SEQ ID NOS: 49

<210> SEQ ID NO 1
<211> LENGTH: 10
<212> TYPE: PRT
<213> ORGANISM: Artificial Sequence
<220> FEATURE:
<223> OTHER INFORMATION: Peptide w
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
```

-continued

```
<221> NAME/KEY: MISC_FEATURE
<222> LOCATION: (10)...(10)
<223> OTHER INFORMATION: NHEt or NH2 or DAla.NH2 or a group which
      removes the charge on the C-terminal amino acid residue

<400> SEQUENCE: 1

Xaa His Trp Ser His Arg Trp Tyr Pro Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide x
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z wherein Z is a group which removes the charge on the
      C-terminal amino acid residue, for example, NH2 or NHEt

<400> SEQUENCE: 2

Xaa His Trp Ser His Arg Trp Tyr Pro Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Peptide y
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z wherein Z is a group which removes the charge on the
      C-terminal amino acid residue, for example, NH2 or NHEt

<400> SEQUENCE: 3

Xaa His Trp Ser His Arg Leu Arg Pro Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Peptide z
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
```

```
<222> LOCATION: (6)..(6)
<223> OTHER INFORMATION: D-isomeric form
<220> FEATURE:
<221> NAME/KEY: MISC_FEATURE
<222> LOCATION: (10)..(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z wherein Z is a group which removes the charge on the
      C-terminal amino acid residue, for example, NH2 or NHEt

<400> SEQUENCE: 4

Glu His Trp Ser His Ser Trp Tyr Pro Xaa
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Peptide w1
<220> FEATURE:
<221> NAME/KEY: MISC_FEATURE
<222> LOCATION: (1)..(1)
<223> OTHER INFORMATION: Pyroglutamate
<220> FEATURE:
<221> NAME/KEY: MISC_FEATURE
<222> LOCATION: (6)..(6)
<223> OTHER INFORMATION: D-isomeric form
<220> FEATURE:
<221> NAME/KEY: MISC_FEATURE
<222> LOCATION: (9)..(9)
<223> OTHER INFORMATION: COOH terminal group replaced with NH2

<400> SEQUENCE: 5

Xaa His Trp Ser His Arg Trp Tyr Pro
1               5

<210> SEQ ID NO 6
<211> LENGTH: 10
<212> TYPE: PRT
<213> ORGANISM: Artificial Sequence
<220> FEATURE:
<223> OTHER INFORMATION: Peptide x1
<220> FEATURE:
<221> NAME/KEY: MISC_FEATURE
<222> LOCATION: (1)..(1)
<223> OTHER INFORMATION: Pyroglutamate
<220> FEATURE:
<221> NAME/KEY: MISC_FEATURE
<222> LOCATION: (6)..(6)
<223> OTHER INFORMATION: D-isomeric form
<220> FEATURE:
<221> NAME/KEY: MISC_FEATURE
<222> LOCATION: (10)..(10)
<223> OTHER INFORMATION: COOH terminal group replaced with NH2

<400> SEQUENCE: 6

Xaa His Trp Ser His Arg Trp Tyr Pro Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: peptide y1
<220> FEATURE:
<221> NAME/KEY: MISC_FEATURE
<222> LOCATION: (1)..(1)
<223> OTHER INFORMATION: Pyroglutamate
<220> FEATURE:
<221> NAME/KEY: MISC_FEATURE
<222> LOCATION: (6)..(6)
```

```
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 7

Xaa His Trp Ser His Arg Leu Arg Pro Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Peptide z1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 8

Xaa His Trp Ser His Ser Trp Tyr Pro Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Peptide 1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (5)...(8)
<223> OTHER INFORMATION: Amino acids 5, 7 and 8 are respectively "His,
      Leu and Arg" or "Tyr, Trp and Arg" or "Tyr, Leu and Tyr" or "His,
      Trp and Arg" or "His Leu and Tyr" or "Tyr, Trp and Tyr"
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 9

Xaa His Trp Ser Xaa Gly Xaa Xaa Pro Xaa
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Peptide 2
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
```

```
<222> LOCATION: (5)..(5)
<223> OTHER INFORMATION: Tyr or His
<220> FEATURE:
<221> NAME/KEY: MISC_FEATURE
<222> LOCATION: (7)..(7)
<223> OTHER INFORMATION: Leu/Trp
<220> FEATURE:
<221> NAME/KEY: MISC_FEATURE
<222> LOCATION: (8)..(8)
<223> OTHER INFORMATION: Any amino acid except arginine
<220> FEATURE:
<221> NAME/KEY: MISC_FEATURE
<222> LOCATION: (10)..(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 10

Xaa His Trp Ser Xaa Gly Xaa Xaa Pro Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Peptide a1
<220> FEATURE:
<221> NAME/KEY: MISC_FEATURE
<222> LOCATION: (1)..(1)
<223> OTHER INFORMATION: Pyroglutamate
<220> FEATURE:
<221> NAME/KEY: MISC_FEATURE
<222> LOCATION: (10)..(10)
<223> OTHER INFORMATION: COOH terminal group replaced with NH2

<400> SEQUENCE: 11

Xaa His Trp Ser His Gly Leu Arg Pro Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Peptide b1
<220> FEATURE:
<221> NAME/KEY: MISC_FEATURE
<222> LOCATION: (1)..(1)
<223> OTHER INFORMATION: Pyroglutamate
<220> FEATURE:
<221> NAME/KEY: MISC_FEATURE
<222> LOCATION: (10)..(10)
<223> OTHER INFORMATION: COOH terminal group replaced with NH2

<400> SEQUENCE: 12

Xaa His Trp Ser Tyr Gly Trp Arg Pro Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Peptide c1
<220> FEATURE:
<221> NAME/KEY: MISC_FEATURE
<222> LOCATION: (1)..(1)
<223> OTHER INFORMATION: Pyroglutamate
<220> FEATURE:
<221> NAME/KEY: MISC_FEATURE
<222> LOCATION: (10)..(10)
```

<223> OTHER INFORMATION: COOH terminal group replaced with NH2

<400> SEQUENCE: 13

Xaa His Trp Ser Tyr Gly Leu Tyr Pro Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Peptide d1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 14

Xaa His Trp Ser His Gly Trp Arg Pro Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Peptide e1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 15

Xaa His Trp Ser His Gly Leu Tyr Pro Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Peptide f1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 16

Xaa His Trp Ser Tyr Gly Trp Tyr Pro Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Peptide 3
<220> FEATURE:
<221> NAME/KEY: MISC_FEATURE

```
<222> LOCATION: (1)...(1)
<223> OTHER INFORMATION: Pyroglutamate
<220> FEATURE:
<221> NAME/KEY: MISC_FEATURE

```
<213> ORGANISM: Artificial Sequence
<220> FEATURE:
<223> OTHER INFORMATION: Peptide iii
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 20

Xaa His Trp Ser Tyr Lys Trp Gln Pro Xaa
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Peptide iv
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 21

Xaa His Trp Ser Tyr Lys Trp Leu Pro Xaa
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Peptide v
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 22

Xaa His Trp Ser Tyr Lys Trp Tyr Pro Xaa
1               5                   10
```

<210> SEQ ID NO 23
<211> LENGTH: 10
<212> TYPE: PRT
<213> ORGANISM: Artificial Sequence
<220> FEATURE:
<223> OTHER INFORMATION: Peptide vB
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 23

Xaa His Trp Ser Tyr Lys Trp Arg Pro Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Peptide vi
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 24

Xaa His Trp Ser Tyr Trp Trp Arg Pro Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Peptide vii
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

```
<400> SEQUENCE: 25

Xaa His Trp Ser His Lys Trp Tyr Pro Xaa
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Peptide viii
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: NHEt or NH2 or DAla.NH2 or Z, wherein Z is a
      group which removes the charge on the C-terminal amino acid
      residue, for example, NH2 or NHEt

<400> SEQUENCE: 26

Xaa His Trp Ser His Arg Trp Tyr Pro Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Peptide ix
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 27

Xaa His Trp Ser His Arg Leu Arg Pro Xaa
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Peptide x
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
```

-continued

<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 28

Xaa His Trp Ser His Trp Trp Arg Pro Xaa
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Peptide xi
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 29

Xaa His Trp Ser His Trp Leu Arg Pro Xaa
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Peptide xii
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 30

Xaa His Trp Ser His Tyr Leu Arg Pro Xaa
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Peptide xiii
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE

```
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 31

Xaa His Trp Ser His Ala Trp Tyr Pro Xaa
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Peptide xiv
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: Z or azaGly or azaGly.Z or DAla.Z or Glu.Z or
      DAla-Glu.Z or DAla-DAla.Z or ?Ala.Z or Pro or Pro.Z or DAla-Gly.Z
      or Gly.Z, wherein Z is a group which removes the charge on the
      C-terminal amino acid residue, for example, NH2 or NHEt

<400> SEQUENCE: 32

Xaa His Trp Ser His Ser Trp Tyr Pro Xaa
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Peptide i-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 33

Xaa His Trp Ser His Arg Trp Tyr Pro Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Peptide ii-1
<220> FEATURE:
<221> NAME/KEY: MISC_FEATURE
<222> LOCATION: (1)...(1)
<223> OTHER INFORMATION: Pyroglutamate
```

```
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 34

Xaa His Trp Ser His Trp Trp Tyr Pro Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Peptide iii-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 35

Xaa His Trp Ser Tyr Lys Trp Gln Pro Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Peptide iv-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 36

Xaa His Trp Ser Tyr Lys Trp Leu Pro Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Peptide v-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
```

```
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 37

Xaa His Trp Ser Tyr Lys Trp Tyr Pro Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Peptide v-2
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 38

Xaa His Trp Ser Tyr Lys Trp Arg Pro Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Peptide vi-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 39

Xaa His Trp Ser Tyr Trp Trp Arg Pro Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Peptide vii-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2
```

<400> SEQUENCE: 40

Xaa His Trp Ser His Lys Trp Tyr Pro Gly
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Peptide viii-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (9)...(9)
<223> OTHER INFORMATION: COOH terminal group replaced with NH2

<400> SEQUENCE: 41

Xaa His Trp Ser His Arg Trp Tyr Pro
1               5

<210> SEQ ID NO 42
<211> LENGTH: 10
<212> TYPE: PRT
<213> ORGANISM: Artificial Sequence
<220> FEATURE:
<223> OTHER INFORMATION: Peptide ix-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 42

Xaa His Trp Ser His Arg Leu Arg Pro Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Peptide x-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 43

Xaa His Trp Ser His Trp Trp Arg Pro Gly

```
1               5                  10

<210> SEQ ID NO 44
<211> LENGTH: 10
<212> TYPE: PRT
<213> ORGANISM: Artificial Sequence
<220> FEATURE:
<223> OTHER INFORMATION: Peptide xi-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 44

Xaa His Trp Ser His Trp Leu Arg Pro Gly
1               5                  10

<210> SEQ ID NO 45
<211> LENGTH: 10
<212> TYPE: PRT
<213> ORGANISM: Artificial Sequence
<220> FEATURE:
<223> OTHER INFORMATION: Peptide xii-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 45

Xaa His Trp Ser His Tyr Leu Arg Pro Gly
1               5                  10

<210> SEQ ID NO 46
<211> LENGTH: 10
<212> TYPE: PRT
<213> ORGANISM: Artificial Sequence
<220> FEATURE:
<223> OTHER INFORMATION: Peptide xiii-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 46

Xaa His Trp Ser His Ala Trp Tyr Pro Gly
1               5                  10

<210> SEQ ID NO 47
```

```
<211> LENGTH: 10
<212> TYPE: PRT
<213> ORGANISM: Artificial Sequence
<220> FEATURE:
<223> OTHER INFORMATION: Peptide xiv-1
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (6)...(6)
<223> OTHER INFORMATION: D-isomeric form
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 47

Xaa His Trp Ser His Ser Trp Tyr Pro Gly
1               5                   10

<210> SEQ ID NO 48
<211> LENGTH: 10
<212> TYPE: PRT
<213> ORGANISM: Homo sapiens
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 48

Xaa His Trp Ser Tyr Gly Leu Arg Pro Gly
1               5                   10

<210> SEQ ID NO 49
<211> LENGTH: 10
<212> TYPE: PRT
<213> ORGANISM: Homo sapiens
<220> FEATURE:
<221> NAME/KEY: MISC_FEATURE
<222> LOCATION: (1)...(1)
<223> OTHER INFORMATION: Pyroglutamate
<220> FEATURE:
<221> NAME/KEY: MISC_FEATURE
<222> LOCATION: (10)...(10)
<223> OTHER INFORMATION: COOH terminal group replaced with NH2

<400> SEQUENCE: 49

Xaa His Trp Ser His Gly Trp Tyr Pro Gly
1               5                   10
```

METHODS OF TREATING REPRODUCTIVE CANCER

This application is the U.S. National Stage of International Application No. PCT/GB2007/001586, filed May 1, 2007, published in English, and claims priority under 35 U.S.C § 119 or 365 to Great Britain Application No. 0616111.1, filed Aug. 12, 2006 and claims the benefit of U.S. Application No. 60/805,042, filed Jun. 16, 2006 and U.S. Application 60/805,181, filed Jun. 19, 2006.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 24,710 byte ASCII(text) file named "Seq_List" created on Dec. 16, 2008.

The present invention relates to agents, compositions and methods for use in medicine. In particular, the invention relates to agents related to GnRH peptides.

At least two forms of gonadotropin-releasing hormone (GnRH) exist in humans. While the biological actions of GnRH II are poorly defined, we know that GnRH I is the central regulator in the neuroendocrine control of mammalian reproduction. GnRH I released from hypothalamic neurons binds its specific, G protein-coupled receptor (GPCR) in the anterior pituitary, ultimately stimulating the synthesis and release of gonadotropins (Kaiser et al., 1997; Millar et al., 2004). GnRHs have additional effects on extra-pituitary tissues and several types of cancers, particularly those of the reproductive system. mRNA of the hormones and the receptor have been found in these tumours and a direct inhibition of cell growth by GnRH has been shown in vitro and in vivo (reviewed in (Limonta et al., 2003) and Grundker et al., 2002). Investigation into this novel action is quite recent and has resulted in a contradictory collection of data. For example, the finding of two distinct binding sites and a pharmacologically different receptor in tumoural cells has led to some researchers to propose the existence of a second subtype of receptor (named type II as opposed to the type I pituitary one) (Enomoto et al., 2004; Grundker et al., 2004; Neill et al., 2004). However, although a type II receptor has been cloned in some primates, a functional alternative subtype has not yet been found in humans (Morgan et al., 2003). Moreover, the mRNA and cDNA found in gynaecological cancers correspond to the type I receptor (Limonta et al., 2003).

The molecular mechanism whereby GnRH mediates its antiproliferative action is also a matter of debate. Some evidence shows that the receptor expressed in tumours is primarily coupled to Gi, unlike the pituitary receptor, which is coupled to Gq (Grundker et al., 2002; Limonta et al., 2003). Other multiple intracellular pathways have been named to be activated, including down-regulation of growth factor actions (by decrease of expression of growth factors and their receptors and activation of phosphotyrosine phosphatase), inhibition of Akt and the 60s acidic ribosomal phosphoproteins (restraining cell survival and protein synthesis, respectively) and activation of several mitogen-activated protein kinases (MAPKs) (Grundker 2001; Chen et al., 2002 Kim et al., 2004b; Kimura et al., 1999; Kraus et al., 2004 Tanaka et al., 2003). The outcome of GnRH exposure upon the regulation of cell growth is unquestionably determined by the cell type (dictating intracellular content and steroid hormone dependency for proliferation), the regime of treatment and other, sometimes obscure, factors.

GB 2,237,571 A relates to gonadotropin releasing hormone analogues. Folkers et al. (1985, *Proc. Natl. Acad. Sci. USA.*, 82:1070-1074) relates to decapeptides biologically equivalent to the luteinizing hormone-releasing hormone. Millar et al. (1989, *J. Biol. Chem.*, 35:21007-21013) relates to chimeric analogues of vertebrate gonadotropin-releasing hormones.

GnRH peptides have previously been administered to treat proliferative disorders, such as cancers, by modulating release of hormones by the pituitary gland. However, it has recently been demonstrated that antiproliferation is also an inherent characteristic of the ligand, which is able to preferentially activate a particular signalling cascade, an occurrence termed ligand-induced selective signalling (LISS) (Maudsley et al., 2004; Millar & Pawson, 2004). This explains how ligands characterized as antagonists because they do not activate pituitary receptors can convey cell growth suppression of other cell types through the same receptor. To date, very few ligands with these properties have been identified.

The present inventors have determined the structural requirements of the GnRH I and GnRH II peptides that are involved in cell-growth suppression and have surprisingly discovered that the antiproliferative activity of the GnRH I and GnRH II peptides can be modulated by substituting specific amino acid residues in the peptide sequence.

The peptide sequence of human GnRH I is (displayed using the three-letter code for amino acid residues): pGlu-His-Trp-Ser-Tyr-Gly-Leu-Arg-Pro-Gly.NH$_2$.

The peptide sequence of human GnRH II is (displayed using the Three-letter code for amino acid residues): pGlu-His-Trp-Ser-His-Gly-Trp-Tyr-Pro-Gly.NH$_2$.

In particular, the inventors have discovered that substituting amino acid residues at positions 5 and/or 7 and/or 8 of the GnRH I peptide sequence, and particularly removal of the arginine residue at position 8, results in elevated antiproliferative activity. Furthermore, the introduction of certain D-amino acid residues at position 6 of the GnRH II peptide sequence results in elevated antiproliferative activity. This surprising discovery provides potent and selective agents for use in treating antiproliferative disorders, such as cancer.

Accordingly, in a first aspect, the invention provides an agent comprising the peptide sequence:

pGlu-His-Trp-Ser-R1-Gly-R2-R3-Pro-A wherein:
a) R1 is His, R2 is Leu and R3 is Arg; or
b) R1 is Tyr, R2 is Trp and R3 is Arg; or
c) R1 is Tyr, R2 is Leu and R3 is Tyr; or
d) R1 is His, R2 is Trp and R3 is Arg; or
e) R1 is His, R2 is Leu and R3 is Tyr; or
f) R1 is Tyr, R2 is Trp and R3 is Tyr
and wherein A is selected from the group consisting of:
Z; or
azaGly; or
azaGly.Z; or
DAla.Z; or
Glu. Z; or
DAla-Glu.Z; or
DAla-DAla.Z; or
βAla.Z; or
Pro; or
Pro.Z
DAla-Gly.Z; and
Gly.Z, wherein Z is a group which removes the charge on the C-terminal amino acid residue
for use in medicine.

Preferably, Z has a molecular weight of less than 200, preferably less than 150, preferably less than 100. Preferably, Z is NHR' wherein R' is H or $C_1$ to $C_4$ alkyl or Z is OR" wherein R" is $C_1$ to $C_4$ alkyl. Preferably, Z is an amide. Preferably, Z is $NH_2$ or N-propylamide or N-ethylamide (NHEt) or N-methylamide or N-butylamide.

The abbreviation "pGlu" represents the modified amino acid, pyroglutamate.

Preferably, A is azaGly.$NH_2$. The abbreviation "azaGly" represents azaglycine, in which the C—H group is replaced by a nitrogen atom. The abbreviation "azaGly.$NH_2$" represents an amidated form of azaglycine.

Preferably, A is DAla.$NH_2$ or Glu.$NH_2$. The abbreviations "DAla.$NH_2$" and "Glu.$NH_2$" represent an amidated form of the D-alanine residue and glutamate residue, respectively.

Preferably, A is DAla-Glu.$NH_2$ or DAla-DAla.$NH_2$ or DAla-Gly.$NH_2$.

Preferably, A is βAla.$NH_2$. The abbreviation "βAla" represents β-alanine, a modified form of alanine in which the amino group is at the β (beta)-position relative to the carboxyl group. The abbreviation "βAla.$NH_2$," represents an amidated form of β-alanine.

Preferably, A is Pro.Z wherein Z is selected from the group consisting of $NH_2$, N-propylamide, N-ethylamide, N-methylamide and N-butylamide.

The abbreviation "Gly.$NH_2$" represents an amidated form of the glycine residue. Preferably, the agents of the invention possess a C-terminal residue that is uncharged at its C-terminus, which may be achieved by modification with a C-terminal group such as $NH_2$, or NHEt (N-ethlyamide).

By "an agent" we include salts (e.g. organic or inorganic acid addition salts), esters and solvates of the molecules comprising or consisting of the peptide sequences of the invention. It will be appreciated that the term further includes derivatives that have the same biological function and/or activity as the relevant agent. Moreover, for the purposes of this invention, the term also includes prodrugs of the relevant agent (for example, esters). The term "prodrug" includes any composition of matter that, following oral or parenteral administration, is metabolised in vivo to form the relevant agent in an experimentally-detectable amount, and within a predetermined time of dosing.

Preferably, the agents of the invention are capable of reversibly or irreversibly binding to the GnRH receptor and preferably capable of selectively binding to the GnRH receptor. By "selectively binding" we include the ability of the agents of the invention to bind at least 10-fold more strongly to the GnRH receptor than to another polypeptide; preferably at least 50-fold more strongly and more preferably at least 100-fold more strongly. Preferably, the agents of the invention bind to the GnRH receptor under physiological conditions, for example, in vivo.

The agents of the invention may further consist of or comprise one or more moiety which is capable of targeting and/or localising the agent of the invention to a target cell (such as a cancer cell) and/or to increase the half-life (t½) of the agent of the invention. Such moieties can therefore increase efficacy of the agents of the invention. Preferably, one or more moiety may be included in an agent of the invention when the agent comprises or consists of a peptide sequence comprising a D-amino acid (preferably D-Lys or D-Glu or D-Asp or D-Cys) at position 6 of the peptide sequence, as those amino acid residues are particularly amenable to modification.

Preferably, the one or more moiety is a steroid hormone molecule (including, for example, progesterone, testosterone, estradiol or corticol) and is conjugated to the side chain of a D-amino acid. Steroid hormone molecules are capable of binding to plasma proteins and have been shown to reduce the metabolic clearance of GnRH peptides (Ratcliffe et al., 2006, *Endocrinology*, 147:571-9). GnRH peptides conjugated to steroid hormones are described in WO2004/08725, incorporated herein by reference. Alternatively, the one or more moiety is a vitamin, such as vitamin B12 or vitamin D, and is conjugated to the side chain of a D-amino acid. Vitamins have been shown to improve the oral bioavailability of GnRH peptides (Russell-Jones et al., 1995, Bioconjug. Chem., 6:34-42; Russell-Jones et al., 1995, Bioconjug. Chem., 6:459-465).

Preferably, the ability of the agent of the invention to bind to and activate the GnRH receptor is not affected and/or significantly affected by the one or more moiety.

Several factors determine the antiproliferative activity of the agents of the invention, including the affinity of the agent for the GnRH receptor and the coupling of the receptor to the intracellular machinery involved in the parturition signalling pathway. Thus, the antiproliferative activity of the agents of the invention is not determined solely by its affinity for the GnRH receptor—for example, two agents of the invention may display different antiproliferative activities but have identical affinities for the GnRH receptor.

The GnRH receptor is a G protein-coupled receptor (GPCR) that possesses seven-transmembrane domains (7™). Cloning and characterisation of such receptors are described, for example, in Tsutsumi et al. (1992, *Mol. Endocrinol.,* 6:1163-1169) and Kakar et al. (1992, *Biochem. Biophys. Res. Comm.,* 189:289-295) and Chi et al. (1993, *Mol. Cell. Endocrinol.,* 91:R1-6).

Methods for determining the binding of a GnRH peptide (or analogue thereof) to the GnRH receptor include a competitive binding assay as described in Tsutsumi et al. (1992, *Mol. Endocrinol.,* 6:1163-1169) and Kakar et al. (1992, *Biochem. Biophys. Res. Comm.,* 189:289-295) and Chi et al. (1993, *Mol. Cell. Endocrinol.,* 91:R1-6). Briefly, in that method, the peptide or analogue of interest is labelled with $I^{125}$ and binding determined in the presence of an unlabelled peptide in whole cells expressing the GnRH receptor or membranes comprising the GnRH receptor.

In a second aspect, the invention provides an agent comprising the peptide sequence:

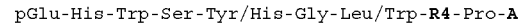

pGlu-His-Trp-Ser-Tyr/His-Gly-Leu/Trp-R4-Pro-A wherein: R4 is any amino acid except arginine
and A is selected from the group consisting of:
Z; or
azaGly; or
azaGly.Z; or
DAla.Z; or
Glu.Z; or
DAla-Glu.Z; or
DAla-DAla.Z; or
βAla.Z; or
Pro; or
Pro.Z; or
DAla-Gly.Z; and
Gly.Z,
wherein Z is a group which removes the charge on the C-terminal amino acid residue
for use in medicine.

Preferably, Z has a molecular weight of less than 200, preferably less than 150, preferably less than 100. Preferably, Z is NHR' wherein R' is H or $C_1$ to $C_4$ alkyl or Z is OR" wherein R" is $C_1$ to $C_4$ alkyl. Preferably, Z is an amide. Preferably, Z is $NH_2$ or N-propylamide or N-ethylamide (NHEt) or N-methylamide or N-butylamide.

By Tyr/His we include that either the amino acid Tyrosine (Tyr) or the amino acid Histidine (His) is present at position 5 of the peptide sequence.

By Leu/Trp we include that either the amino acid Leucine (Leu) or the amino acid Tryptophan (Trp) is present at position 7 of the peptide sequence.

Preferably, A is azaGly.$NH_2$.
Preferably, A is DAla.$NH_2$ or Glu.$NH_2$.
Preferably, A is DAla-Glu.$NH_2$ or DAla-DAla.$NH_2$ or DAla-Gly.$NH_2$.
Preferably, A is βAla.$NH_2$.
Preferably, A is Pro.Z wherein Z is selected from the group consisting of $NH_2$, N-propylamide, N-ethylamide, N-methylamide and N-butylamide.

Preferably, the invention provides an agent wherein R4 is selected from the group comprising: alanine; asparagine; cysteine; aspartic acid; glutamic acid; phenylalanine; glycine; histidine; isoleucine; lysine; leucine; methionine; proline; glutamine; serine; threonine; valine; tryptophan; tyrosine.

The term "amino acid" includes any of a group of water-soluble organic compounds that possess both a carboxyl (—COOH) and an amino (—$NH_2$) group attached to the α-carbon atom. Amino acids can be represented by the general formula R—CH($NH_2$)COOH; the R group is hydrogen or an organic group and determines the properties of any particular amino acid. The tetrahedral array of four different groups about the α-carbon atom confers optical activity on amino acids. The two-mirror image forms are called an L-isomer and a D-isomer. Typically, only L-amino acids are constituents of proteins. Preferably, the GnRH-receptor-binding moiety of the agents of the first and second aspects of the invention consist of L-amino acids.

Through the formation of peptide bonds, amino acids join together to form short chains (peptides) or longer chains (polypeptides). It is well known that proteins are composed of varying proportions of approximately 20 commonly-occurring amino acids, the sequence of which determines the shape, properties and biological role of the protein. Amino acid residues within such peptide or polypeptide chains are conventionally referred to by their numbered position in the chain, with the first position (i.e. position 1) assigned to the amino acid at the N-terminal end of the chain.

In a third aspect, the invention provides the use of an agent comprising or consisting of the peptide sequence: pLGlu-LHis-LTrp-LSer-LHis-X-LTrp-LTyr-LPro-A, wherein X is a D-amino acid residue and A is selected from the group consisting of:
Z; or
azaGly; or
azaGly.Z; or
DAla.Z; or
Glu.Z; or
DAla-Glu.Z; or
DAla-DAla.Z; or
βAla.Z; or
Pro; or
Pro.Z; or
DAla-Gly.Z; and
Gly.Z,
wherein Z is a group which removes the charge on the C-terminal amino acid residue in the manufacture of a medicament for treating a proliferative disorder.

Preferably, the invention provides an use wherein X is selected from the group comprising: D-arginine; D-lysine; D-tryptophan; D-lysine; D-tyrosine; D-alanine; D-serine.

Preferably, A is azaGly.$NH_2$.
Preferably, A is DAla.$NH_2$ or Glu.$NH_2$.
Preferably, A is DAla-Glu.$NH_2$ or DAla-DAla.$NH_2$ or DAla-Gly.$NH_2$.
Preferably, A is βAla.$NH_2$.
Preferably, A is Pro.Z wherein Z is selected from the group consisting of $NH_2$, N-ethylamide, N-propylamide, N-methylamide and N-butylamide.

In a fourth aspect, the invention provides the use of an agent comprising a peptide sequence selected from the group comprising:

i) pLGlu-LHis-LTrp-LSer-LHis-DArg-LTrp-LTyr-LPro-A;

ii) pLGlu-LHis-LTrp-LSer-LHis-DTrp-LTrp-LTyr-LPro-A;

iii) pLGlu-LHis-LTrp-LSer-LTyr-DLys-LTrp-LGln-LPro-A;

iv) pLGlu-LHis-LTrp-LSer-LTyr-DLys-LTrp-LLeu-LPro-A;

v) pLGlu-LHis-LTrp-LSer-LTyr-DLys-LTrp-LTyr-LPro-A;

v-B) pLGlu-LHis-LTrp-LSer-LTyr-DLys-LTrp-LArg-LPro-A;

vi) pLGlu-LHis-LTrp-LSer-LTyr-DTrp-LTrp-LArg-LPro-A;

vii) pLGlu-LHis-LTrp-LSer-LHis-DLys-LTrp-LTyr-LPro-A;

viii) pLGlu-LHis-LTrp-LSer-LHis-DArg-LTrp-LTyr-LPro.Y;

ix) pLGlu-LHis-LTrp-LSer-LHis-DArg-LLeu-LArg-LPro-A;

x) pLGlu-LHis-LTrp-LSer-LHis-DTrp-LTrp-LArg-LPro-A;

xi) pLGlu-LHis-LTrp-LSer-LHis-DTrp-LLeu-LArg-LPro-A;

xii) pLGlu-LHis-LTrp-LSer-LHis-DTyr-LLeu-LArg-LPro-A;

xiii) pLGlu-LHis-LTrp-LSer-LHis-DAla-LTrp-LTyr-LPro-A;

xiv) pLGlu-LHis-LTrp-LSer-LHis-DSer-LTrp-LTyr-LPro-A wherein Y is DAla.$NH_2$ or Z;

and A is selected from the group consisting of:
Z
azaGly; or
azaGly.Z; or
DAla.Z; or
Glu.Z; or
DAla-Glu.Z; or
DAla-DAla.Z; or
βAla.Z; or
Pro; or
Pro.Z; or
DAla-Gly.Z; and
Gly.Z,
  wherein Z is a group which removes the charge on the C-terminal amino acid residue
in the manufacture of a medicament for treating a proliferative disorder.

Preferably, Z has a molecular weight of less than 200, preferably less than 150, preferably less than 100. Preferably, Z is NHR' wherein R' is H or $C_1$ to $C_4$ alkyl or Z is OR" wherein R" is $C_1$ to $C_4$ alkyl. Preferably, Z is an amide. Preferably, Z is $NH_2$ or N-propylamide or N-ethylamide (NHEt) or N-methylamide or N-butylamide.

Preferably, A is azaGly.$NH_2$.
Preferably, A is DAla.$NH_2$ or Glu.$NH_2$.
Preferably, A is DAla-Glu.$NH_2$ or DAla-DAla.$NH_2$ or DAla-Gly.$NH_2$.
Preferably, A is βAla.$NH_2$.
Preferably, A is Pro.Z wherein Z is selected from the group consisting of $NH_2$, N-propylamide, N-ethylamide, N-methylamide and N-butylamide.

One embodiment of peptide (viii) in the list above comprises the amino acid residue Pro.NHEt at position nine of the sequence, which abbreviation represents proline modified by the addition of N-ethylamide at the C-terminus.

It is preferred for peptide (viii) that Y is NHEt. The inventors have discovered that the presence of Pro.NHEt results in a peptide having increased antiproliferative activity.

Preferably, the agents of the third and fourth aspects of the invention consist of L-amino acids, with a D-amino acid at position 6.

The agents of the invention include modified versions of the amino acid sequence of the GnRH I and/or GnRH II peptides. Peptide sequences of the agents of the invention may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

The peptide sequence of the agents of the invention may also be synthesised using liquid phase methodology, which is well known those skilled in the art of chemistry and biochemistry.

The peptide sequence of the agents of the invention may comprise or consist of peptidomimetic compounds. The term "peptidomimetic" refers to a compound that mimics the conformation and desirable features of a particular peptide as a therapeutic agent, but that avoids the undesirable features. For example, morphine is a compound which can be orally administered, and which is a peptidomimetic of the peptide endorphin.

In general, therapeutic applications involving peptides are limited due to lack of oral bioavailability and to proteolytic degradation. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely to be an important contributing factor. The problem is, however, more complicated because it has been recognised that even small, cyclic peptides which are not subject to rapid metabolite inactivation nevertheless exhibit poor oral bioavailability. This is likely to be due to poor transport across the intestinal membrane and rapid clearance from the blood by hepatic extraction and subsequent excretion into the intestine. These observations suggest that multiple amide bonds may interfere with oral bioavailability. It is thought that the peptide bonds linking the amino acid residues in the peptide chain may break apart when the peptide drug is orally administered.

There are a number of different approaches to the design and synthesis of peptidomimetics. In one approach, such as disclosed by Sherman and Spatola, *J. Am. Chem. Soc.*, 112: 433 (1990), one or more amide bonds have been replaced in an essentially isoteric manner by a variety of chemical functional groups. This stepwise approach has met with some success in that active analogues have been obtained. In some instances, these analogues have been shown to possess longer biological half-lives than their naturally-occurring counterparts. Nevertheless, this approach has limitations. Successful replacement of more than one amide bond has been rare. Consequently, the resulting analogues have remained susceptible to enzymatic inactivation elsewhere in the molecule. When replacing the peptide bond it is preferred that the new linker moiety has substantially the same charge distribution and substantially the same planarity as a peptide bond.

Retro-inverso peptidomimetics, in which the peptide bonds are reversed, can be synthesised by methods known in the art, for example such as those described in Méziére et al (1997) *J. Immunol*. 159 3230-3237. This approach involves making pseudopeptides containing changes involving the backbone, and not the orientation of side chains. Retro-inverse peptides, which contain NH—CO bonds instead of CO—NH peptide bonds, are much more resistant to proteolysis. Retro-inverso peptidomimetics of certain GnRH peptides have been synthesised previously (Fromme, 2003, *Endocrinology*, 144:3262-9).

In another approach, a variety of un-coded or modified amino acids such as D-amino acids and N-methyl amino acids have been used to modify mammalian peptides. Alternatively, a presumed bioactive conformation has been stabilised by a covalent modification, such as cyclisation or by incorporation of γ-lactam or other types of bridges. See, for example, Veber et al, *Proc. Natl. Acad. Sci. USA*, 75:2636 (1978) and Thursell et al, *Biochem. Biophys. Res. Comm.*, 111:166 (1983).

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

One approach to the synthesis of cyclic stabilised peptidomimetics is ring closing metathesis (RCM). This method involves steps of synthesising a peptide precursor and contacting it with a RCM catalyst to yield a conformationally-restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), has been to design peptide mimics through the application of the transition state analogue concept in enzyme inhibitor design. For example, it is known that the secondary alcohol of staline mimics the tetrahedral transition state of the scissile amide bond of the pepsin substrate. However, the transition state analogue concept has no apparent relevance to hormone agonist/antagonist design.

For the avoidance of doubt, it is not necessary that the amino acid residues in the peptide sequence are joined by standard peptide bonds. For example, as discussed above, the amino acid residues may be linked by reverse peptide bonds, or they may be joined together by other bonds which mimic the bond distance and spatial orientation of a standard peptide bond.

Peptide sequences of the agents of the invention may be purified following synthesis using methods known in the art, such as HPLC and chromatography.

In a fifth aspect, the invention provides an agent as defined in the third or fourth aspect of the invention for use in medicine. Thus, the agents may be packaged and presented for use as a medicament.

In a sixth aspect, the invention provides the use of an agent according to the first or second aspect of the invention in the manufacture of a medicament for treating a proliferative disorder.

By "proliferative disorder" we include any condition involving cellular proliferation and/or growth at an undesirable rate and/or location in the body of an individual, for example: cancer; reproductive cancer; benign prostatic hyperplasia; endometriosis; uterine fibrosis.

It will be appreciated that, since the agents of the invention are capable of inducing programmed cell death (i.e. apoptosis) and cell cycle arrest, the agents may be used to prevent and/or reduce cell proliferation and therefore be used to treat any condition involving undesirable cell proliferation and/or growth.

Preferably, the proliferative disorder is a cancer of an animal; more preferably, the cancer is a reproductive cancer.

Preferably, the animal is a human, but it may be any mammal such as a domesticated mammal (preferably of agricultural or commercial significance including a chicken; cat; dog; pig; sheep; cow; horse).

More preferably, the cancer is selected from the group comprising: gynaecological cancer; prostate cancer; benign prostatic hyperplasia; endometrial cancer; cervical cancer; ovarian cancer; breast cancer; melanoma; pancreatic cancer; gastric cancer. In particularly preferred embodiments of this aspect of the invention, the cancer is prostate cancer or benign prostatic hyperplasia.

All cancers which express the GnRH receptor could potentially be treated using the agents of the invention. Preferably, the cancer is a reproductive cancer (including prostate, endometrial, cervical, ovarian and breast cancers), all of which express the GnRH receptor. Other cancers that have been shown to express the GnRH receptor include melanoma, pancreatic and gastric cancers, among others. Preferably, the cancer is selected from the group comprising: gynaecological cancer; prostate cancer; benign prostatic hyperplasia; endometrial cancer; cervical cancer; ovarian cancer; breast cancer; melanoma; pancreatic cancer; gastric cancer.

Expression of the GnRH receptor may be induced in cells that do not express the GnRH receptor and/or increased in cells that express the GnRH receptor at a level that is too low to use for therapy using the agents of the invention. Once expression of the GnRH receptor has been induced and/or increased to a level in one or more cell that is suitable for therapy using the agents of the invention, that one or more cell may be treated using an agent of the invention.

Methods for inducing expression of genes in a cell are well known in the art. For example, expression of the GnRH receptor may be induced in a cell by activating one or more transcriptional promoter or element thereof responsible for controlling expression of a genomic copy of the GnRH gene in that cell. Alternatively, a polynucleotide molecule (such as a cDNA or vector) comprising sequence encoding the GnRH receptor (with or without transcriptional and translational elements capable of directing expression of the GnRH receptor) may be introduced into a cell and expressed therein using methods known in the art. For example, a polynucleotide molecule may be introduced into a target cell, such as a cancer cell, by coupling it to a ligand capable of binding to a receptor that is expressed on or in that target cell. For example, a polynucleotide molecule may be introduced into certain cancer cells expressing the EGF (epidermal growth factor) receptor by coupling the polynucleotide molecule to the EGF ligand via a poly-lysine conjugate. Alternatively, a polynucleotide molecule may be introduced into a cell using a viral vector (such as adenovirus) using methods well known to those skilled in the art.

Methods for detecting expression of cellular proteins are well known in the art. Methods suitable for detecting expression of the GnRH receptor include: in situ hybridisation and/or PCR for detecting the presence of mRNA encoding the GnRH receptor; radio-ligand binding for detecting the presence of the GnRH receptor protein; and methods involving antibodies capable of specifically binding to the GnRH receptor (for example, immunoblotting, immunohistochemistry, immunofluorescence, and ELISA).

In a seventh aspect, the invention provides a method for preventing and/or reducing proliferation of one or more cell comprising combining an effective amount of an agent according to the first or second or third or fourth aspect of the invention with one or more cell.

By "effective amount" we include an amount of the agent of the invention that is sufficient to reduce proliferation of one or more cell, such as a cancer cell. An effective amount may be determined in vitro by using the methods described in the Examples (for example, the methods used to monitor cell viability, thymidine incorporation, accumulation of phosphorinositides and ligand binding affinity).

Preferably, the cell is a cell in a human or animal body. More preferably, the animal is any mammal such as a domesticated mammal (preferably of agricultural or commercial significance including a chicken; cat; dog; pig; sheep; cow; horse).

In an eighth aspect, the invention provides an agent comprising a peptide sequence selected from the group comprising:

v) pLGlu-LHis-LTrp-LSer-LHis-DArg-LTrp-LTyr-LPro.
Y;

w) pLGlu-LHis-LTrp-LSer-LHis-DArg-LTrp-LTyr-LPro-A;

x) pLGlu-LHis-LTrp-LSer-LHis-DArg-LLeu-LArg-LPro-A;

y) pLGlu-LHis-LTrp-LSer-LHis-DAla-LTrp-LTyr-LPro-A;

z) pLGlu-LHis-LTrp-LSer-LHis-DSer-LTrp-LTyr-LPro-A wherein Y is DAla.$NH_2$ or Z;
and A is selected from the group consisting of:
Z; or
azaGly; or
azaGly.Z; or
DAla.Z; or
Glu.Z; or
DAla-Glu.Z; or
DAla-DAla.Z; or
βAla.Z; or
Pro; or
Pro.Z; or
DAla-Gly.Z; and
Gly.Z, wherein Z is a group which removes the charge on the C-terminal amino acid residue Preferably, Z has a molecular weight of less than 200, preferably less than 150, preferably less than 100. Preferably, Z is NHR' wherein R' is H or $C_1$ to $C_4$ alkyl or Z is OR" wherein R" is $C_1$ to $C_4$ alkyl. Preferably, Z is an amide. Preferably, Z is $NH_2$ or N-propylamide or N-ethylamide (NHEt) or N-methylamide or N-butylamide.

Preferably, A is azaGly.$NH_2$.
Preferably, A is DAla.$NH_2$ or Glu.$NH_2$.
Preferably, A is DAla-Glu.$NH_2$ or DAla-DAla.$NH_2$ or DAla-Gly.$NH_2$.
Preferably, A is βAla.$NH_2$.
Preferably, A is Pro.Z wherein Z is selected from the group consisting of $NH_2$, N-propylamide, N-ethylamide, N-methylamide and N-butylamide.

In a ninth aspect, the invention provides a pharmaceutical composition comprising a therapeutically effective amount of an agent according to the eighth aspect of the invention and a pharmaceutically-acceptable carrier.

By "therapeutically effective amount" we include an amount of the agent of the invention that is sufficient to prevent and/or reduce proliferation of cells to be treated—for example, cancer cells. An effective amount may be determined in vitro by using the methods described in the accompanying Examples (for example, the methods used to monitor cell viability, thymidine incorporation, accumulation of phosphorinositides and ligand binding affinity). A "therapeutic effect" is any effect that alleviates and/or prevents a condition associated with a disease, illness or condition in an individual and will vary depending on the condition to be treated. Appropriate tests for determining the therapeutic effect of an agent, composition or medicament of the invention in an individual will be known to those skilled in the relevant arts of medicine.

By "pharmaceutically acceptable" is included that the formulation is sterile and pyrogen free. Suitable pharmaceutical carriers are well known in the art of pharmacy. The carrier(s) must be "acceptable" in the sense of being compatible with the agent of the invention and not deleterious to the recipients thereof. Typically, the carriers will be water or saline which will be sterile and pyrogen free; however, other acceptable carriers may be used.

The agents, medicaments and pharmaceutical compositions of the present invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The agents, medicaments and pharmaceutical compositions of the present invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of The agents, medicaments and pharmaceutical compositions of the invention. A device which delivers a pulsed electric field to cells increases the permeability of the cell membranes to the drug, resulting in a significant enhancement of intracellular drug delivery.

The agents, medicaments and pharmaceutical compositions of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the agents, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The agents, medicaments and pharmaceutical compositions of the invention can also be delivered orally. The process employs a natural process for oral uptake of vitamin $B_{12}$ in the body to co-deliver proteins and peptides. By riding the vitamin $B_{12}$ uptake system, the nucleic acids, molecules and pharmaceutical formulations of the invention can move through the intestinal wall. Complexes are synthesised between vitamin $B_{12}$, analogues and the drug that retain both significant affinity for intrinsic factor (IF) in the vitamin $B_{12}$ portion of the complex and significant bioactivity of the active substance of the complex.

The agents, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol 8, 84-87.

Preferably, the medicament and/or pharmaceutical composition of the present invention is a unit dosage containing a daily dose or unit, daily sub-dose or an appropriate fraction thereof, of the active ingredient.

The agents, medicaments and pharmaceutical compositions of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the agents, medicaments and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The agents, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents of the invention may be combined with various sweetening or flavouring agents, colouring matter or dyes, with emulsifying and/or suspending agents and with diluents such as water, ethanol, propylene glycol and glycerin, and combinations thereof.

The agents, medicaments and pharmaceutical compositions of the invention can also be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and compositions may be presented in emit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the agents, medicaments and pharmaceutical compositions of the invention will usually be from 10 µg to 500 mg per adult (i.e. from about 0.1 µg to 5 mg/kg, assuming an adult of 100 kg), administered in single or divided doses.

Thus, for example, the tablets or capsules of the agent of the invention may contain an appropriate dosage of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The agents, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoro ethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a agent of the invention and a suitable powder base such as lactose or starch.

Aerosol or dry powder formulations are preferably arranged so that each metered dose or "puff" contains an appropriate amount of an agent of the invention for delivery to the patient. It will be appreciated that he overall daily dose with an aerosol will vary from patient to patient, and may be administered in a single dose or, more usually, in divided doses throughout the day. The precise dosage will be determined by a physician. Dosage may be similar to that used for the drug Buserelin or Buserelin acetate, a synthetic GnRH analogue used to treat prostate cancer and/or benign prostatic hyperplasia, which is known to those skilled in the art.

Alternatively, the agents, medicaments and pharmaceutical compositions of the invention can be administered in the form of a suppository or pessary, or they may be applied topically in the form of a lotion, solution, cream, ointment or dusting powder. The agents, medicaments and pharmaceutical compositions of the invention may also be transdermally administered, for example, by the use of a skin patch. They may also be administered by the ocular route, particularly for treating diseases of the eye.

For ophthalmic use, the agents, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agents, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the agents, medicaments and pharmaceutical compositions of the invention agents of the invention is the preferred route, being the most convenient.

For veterinary use, the agents, medicaments and pharmaceutical compositions of the invention is administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation.

Advantageously, the formulation is a veterinary formulation.

In a tenth aspect, the invention provided a method for treating cancer comprising or consisting of administering an effective amount of an agent according to the first and/or second and/or third and/or fourth aspect of the invention and/or a pharmaceutical composition according to the eighth aspect of the invention to an individual in need thereof.

Advantageously, the agents of the invention may be targeted to a tumour and/or cancer cell and/or administered directly to a tumour and/or cancer cell. In a particularly preferred embodiment, the cancer is prostate cancer or benign prostatic hyperplasia.

In an eleventh aspect, the invention provides a method for treating a proliferative disorder comprising or consisting of administering an effective amount of an agent according to the first and/or second and/or third and/or fourth aspect of the invention and/or a pharmaceutical composition according to the eighth aspect of the invention to an individual in need thereof.

Preferably, the method for treating a proliferative disorder will be customised or tailored to suit the particular individual and disorder to be treated by the physician responsible for treatment. However, the agents of the invention are advantageous in that they display virtually no side-effect, if any, thereby allowing a common method to be used for treating a range of proliferative disorders.

In a twelfth aspect, the invention provides a method for identifying an individual having one or more cell potentially susceptible to treatment using an agent of the first and/or second and/or third and/or fourth aspect of the invention and/or a pharmaceutical composition according to the eighth aspect of the invention, the method comprising or consisting of the steps of:

a) providing a sample comprising one or more cell from the individual to be tested;
b) combining the sample with an agent according to the first and/or second and/or third and/or fourth aspect of the invention and/or a pharmaceutical composition according to the eighth aspect of the invention;
c) determining the level of proliferation of the one or more cell;
d) identifying an individual having one or more cell potentially susceptible to treatment in the event that the agent and/or pharmaceutical composition prevents and/or reduces proliferation of the one or more cell.

Preferably, the cell is a cancer cell.

It will be understood by those skilled in the relevant arts of molecular and cellular biology that the agent of the invention could be used to identify cells, such as cancer cells, potentially susceptible to treatment using an agent as defined herein and/or a pharmaceutical composition as defined herein. For example, an agent of the invention could be used (in accordance with the methods of the invention and those described in the accompanying Examples) as a diagnostic reagent to detect the presence of one or more GnRH receptor on one or more cell, such as a cancer cell, in a test sample and monitor whether proliferation of the one or more cell is prevented and/or reduced by the agent of the invention. It would be clear to a skilled person that the identification of one or more GnRH receptor on one or more cell and prevention and/or reduction of proliferation of the one or more cell may indicate that such a cell would be susceptible to treatment using the agent and/or medicament and/or pharmaceutical composition of the invention.

Methods for obtaining a sample comprising one or more cell, such as a cancer cell, from an individual to be tested are well known to those skilled in the arts of medicine and surgery. For example, a sample may be obtained by taking a biopsy of a tissue or organ or by aspirating liquid material (such as blood, lymph or peritoneal fluid). Such approaches are used, for example, in screening individuals for breast and ovarian cancer.

In a thirteenth aspect, the invention provides a method of producing an agent according to the first and/or second and/or third and/or fourth aspect of the invention comprising or consisting of the step of chemically synthesising a peptide sequence. Methods by which agents as defined herein may be synthesised include those described above.

Preferred, non-limiting examples which embody certain aspects of the invention will now be described, with reference to the following figures:

FIG. 1A. Effect of GnRH I on cell number after 5 days of continuous treatment of four different HEK293 cell lines expressing GnRHR having or lacking a C-terminal tail and wild-type cells. Viable cells were counted with a haemocytometer after trypan blue incubation. Each curve is the sum of at least three separate experiments in which each point was determined in triplicate, with S.E.M. displayed as error bars. Values were normalised to the number of cells that had been left untreated. (hGnRHR: human GnRHR; hGnRBR/cf-GnRBR: human GnRHR with the catfish GnRHR tail; rGn-RHR: rat GnRHR; rGnRHR/TRHR: rat GnRHR with the rat TRHR tail). Note that addition of the intracellular tail present in all GPCRs except the GnRH receptor ablates the antiproliferative effects of GnRH I.

Figure 1B:
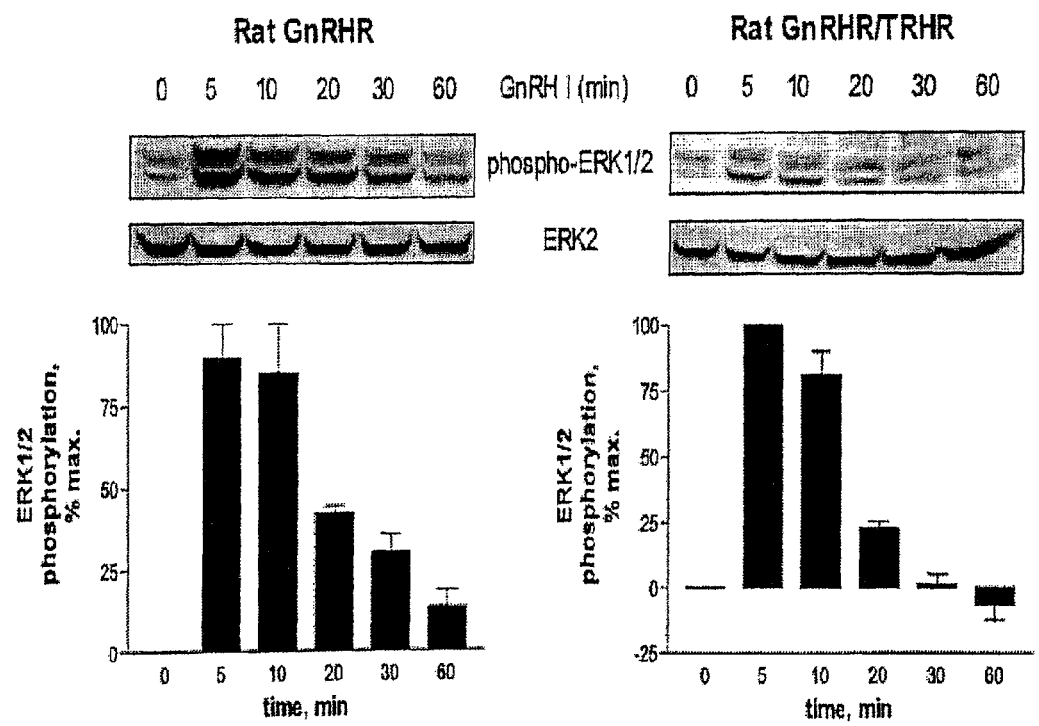

FIG. 1B. ERK activation profiles by 100 nM GnRH I in two HEK293 cell lines, expressing rGnRHR (left) or rGnRHR/TRHR (right). The strips show the signals obtained in whole-cell lysates in a representative western blot using specific anti-phosphorylated ERK1/2 antibody. Each bar in the histograms represents the joined data from at least two independent experiments with S.E.M shown as error bars. Values were normalised to maximal ERK activation within each data set.

Figure 2A:
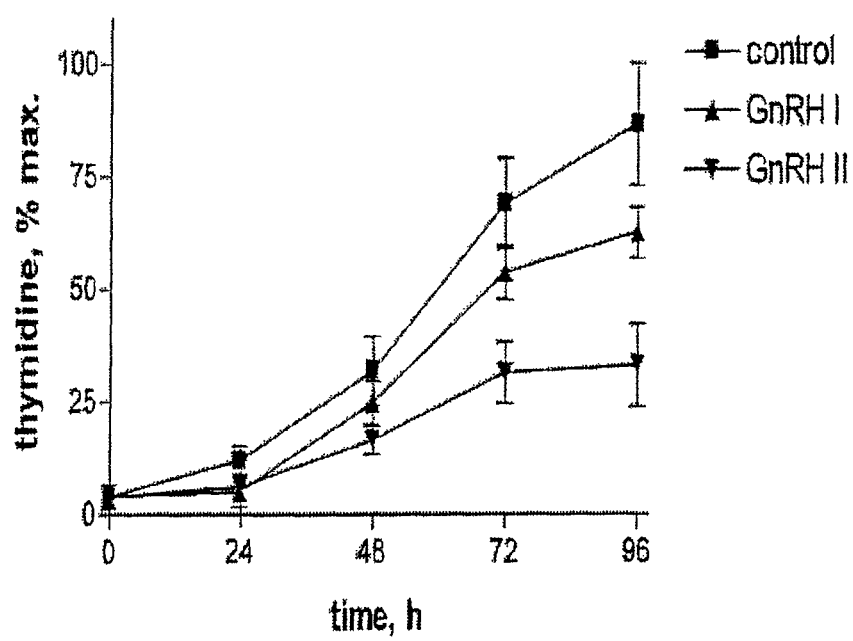

FIG. 2A. Time-course of thymidine incorporation into HEK293/rGnRHR cells exposed to 100 nM of GnRH I or GnRH II. Control cells were left untreated. The graph shown is representative of at least two separate experiments in which each point represents the mean of triplicates with S.E.M. displayed as error bars. Counts were normalised to the maximal thymidine incorporation.

Figure 2B:
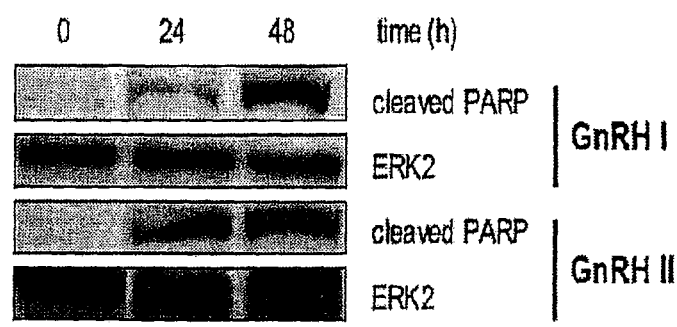

FIG. 2B. Time-course of PARP cleavage (a marker of apoptosis) in HEK293/rGnRHR cells exposed to 100 nM of GnRH I (left) or GnRH II (right). The strips show the signals obtained in whole-cell lysates in a representative western blot using specific anti-cleaved PARP antibody. The data shown are representative of at least two separate experiments.

Figure 3A:
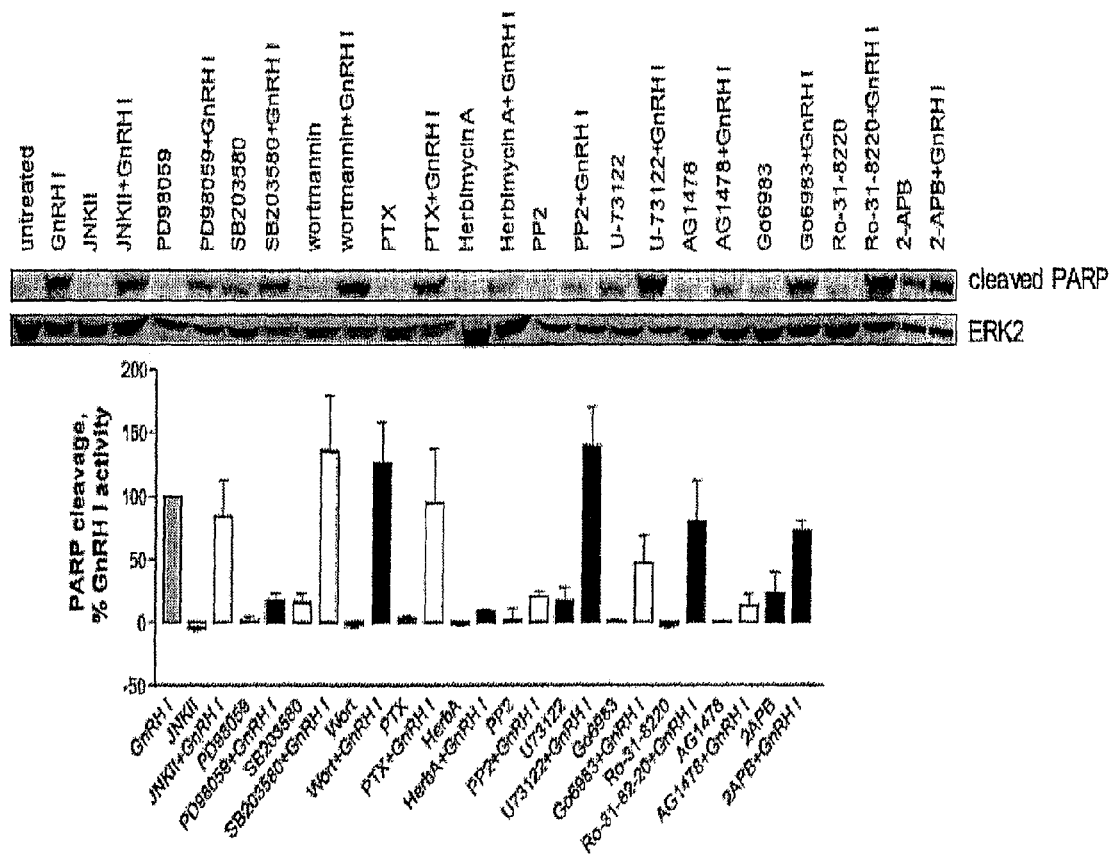
Figure 3B:
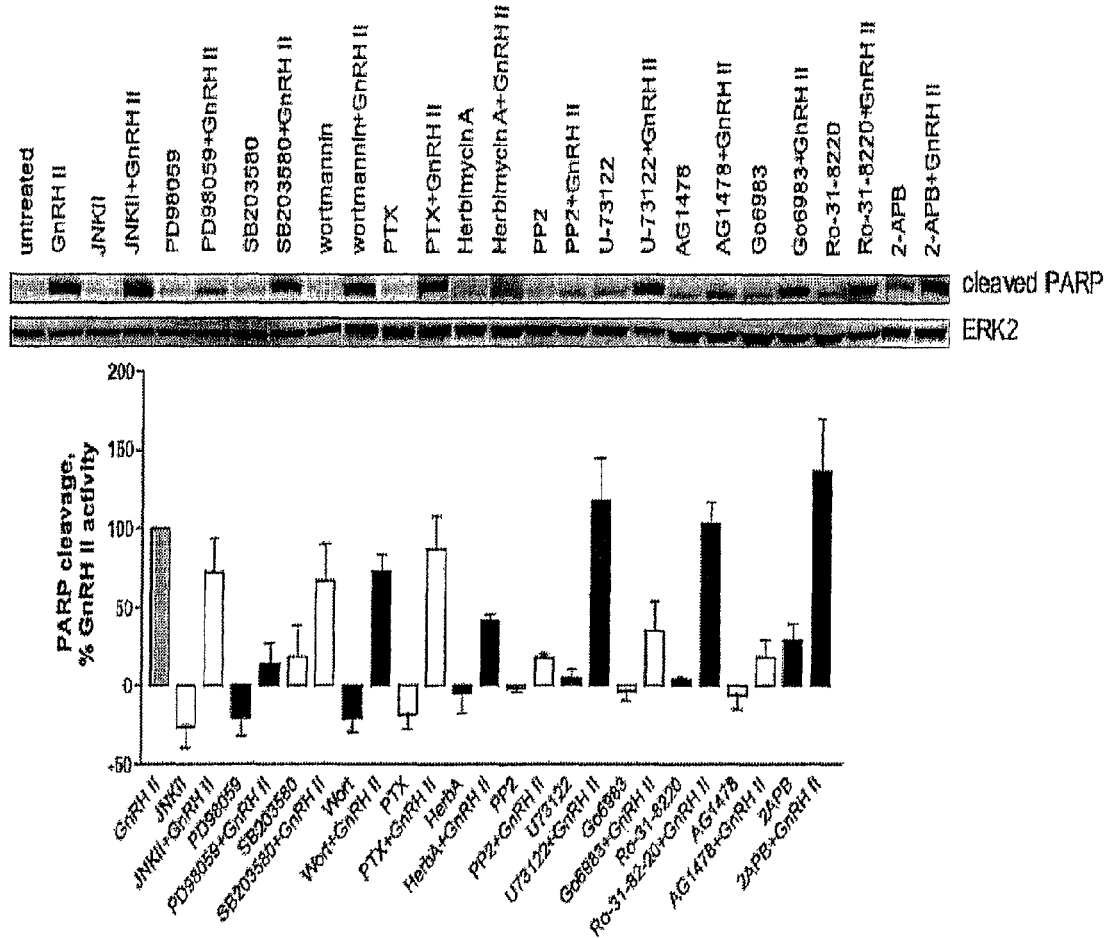

FIGS. 3A and 3B. Inhibition of PARP cleavage induced by GnRH I (FIG. 3A) or GnRH II (FIG. 3B) in HEK293/rGn-RHR cells. Cells were co-treated with 100 nM agonist and different chemical inhibitors (see Methods for individual concentrations) over 48 h in complete medium. Then, crude cell lysate extracts were prepared and cleavage of PARP was determined by specific anti-cleaved PARP antisera immunoblots. Each bar in the histograms represents the joined data from at least three independent experiments with S.E.M shown as error bars.

Figure 4A:
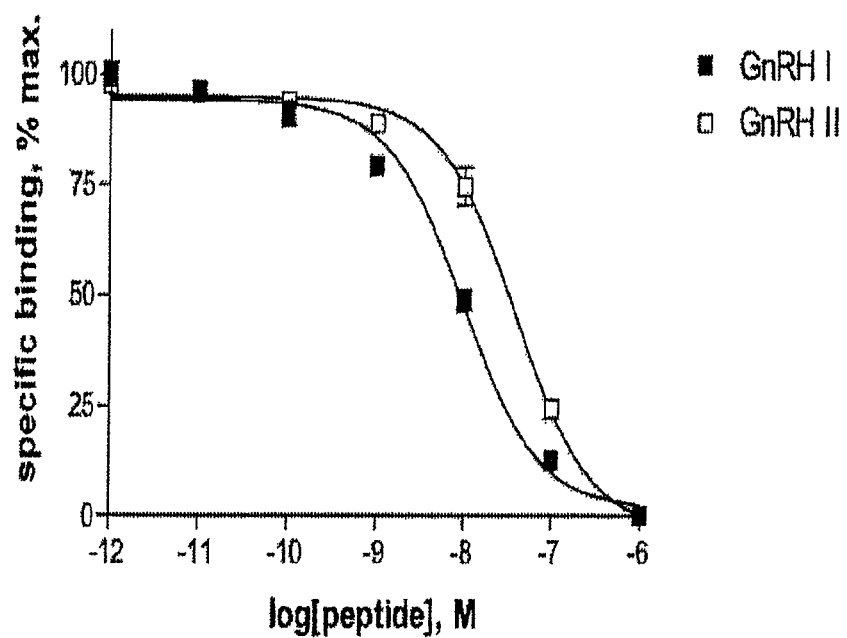

FIG. 4A. Competition binding curves for GnRH I and GnRH II in HEK293/rGnRHR cells. The curves represent one of at least three independent experiments in which each point represents the mean of triplicate values with S.E.M displayed as error bars. Counts were normalised to the maximal specific binding within each data set.

Figure 4B:
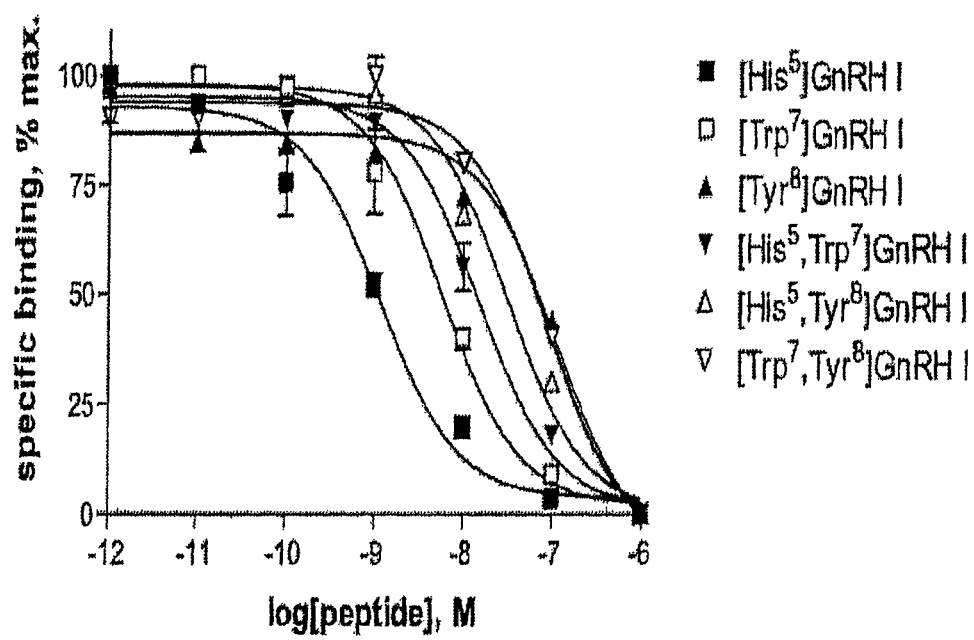

FIG. 4B. Competition binding curves for GnRH analogues in HEK293/rGnRHR cells. The curves represent one of at least three independent experiments in which each point represents the mean of triplicate values with S.E.M displayed as error bars. Counts were normalised to the maximal specific binding within each data set.

Figure 5A:
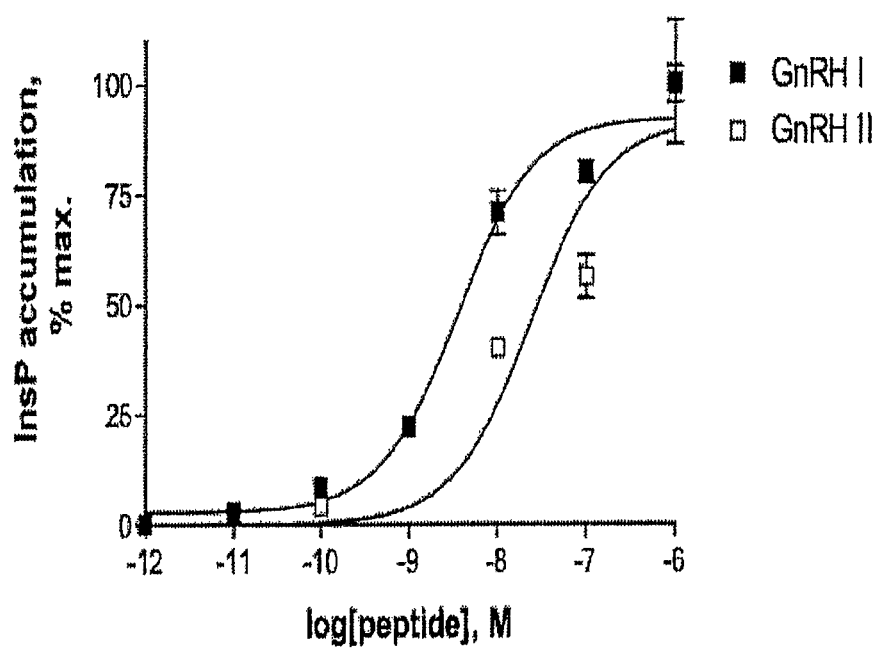

FIG. 5A. Total inositol phosphates accumulation curves for GnRH I and GnRH II in HEK293/rGnRHR cells. The curves represent one of at least three independent experiments in which each point represents the mean of triplicate values with S.E.M displayed as error bars. Counts were normalised to the maximal response within each data set.

Figure 5B:
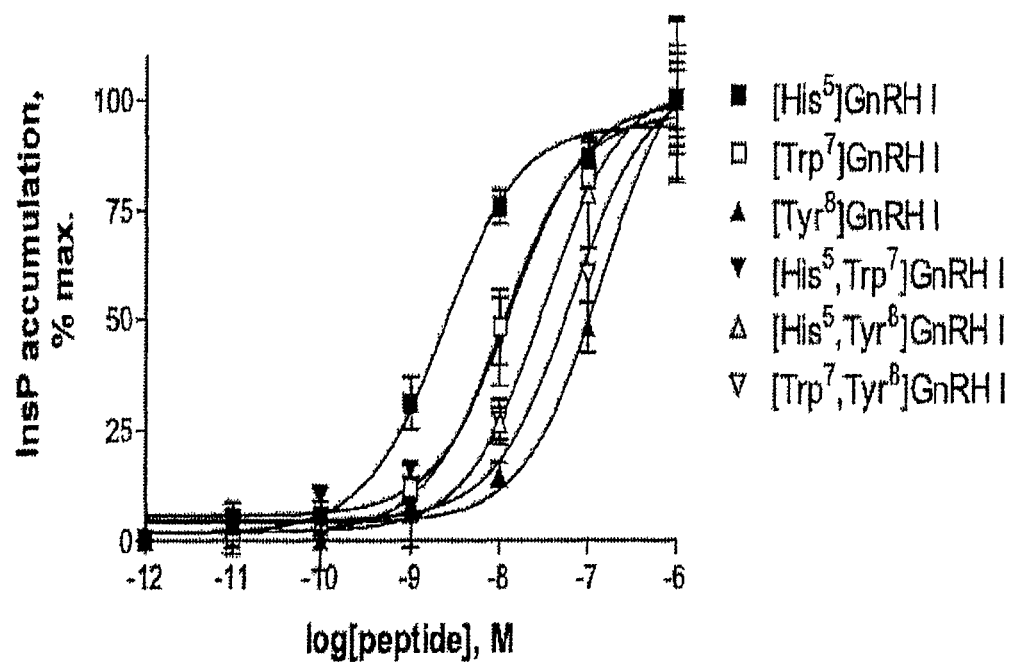

FIG. 5B. Total inositol phosphates accumulation curves for GnRH analogues in HEK293/rGnRHR cells. The curves represent one of at least three independent experiments in which each point represents the mean of triplicate values with S.E.M displayed as error bars. Counts were normalised to the maximal response within each data set.

Figure 6A:
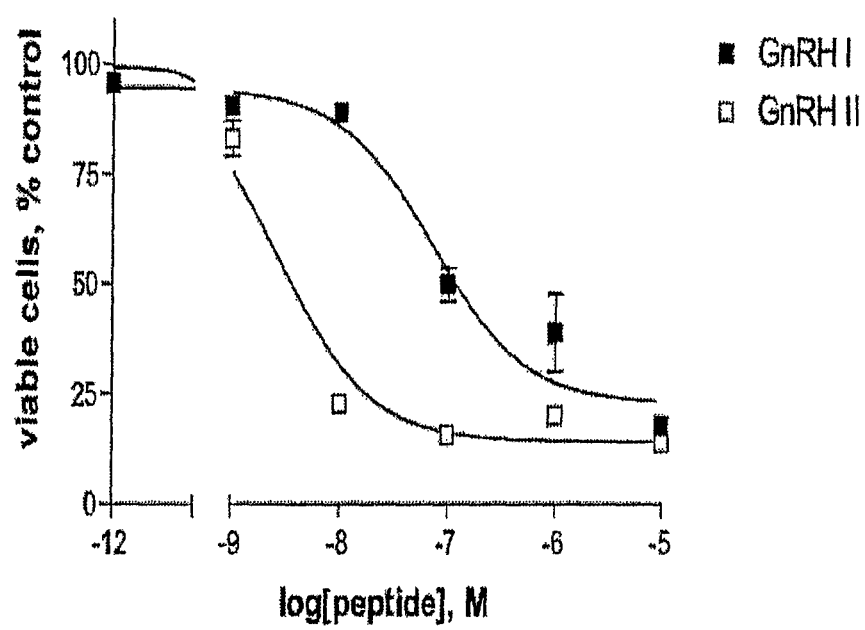

FIG. 6A. Antiproliferation curves for GnRH and GnRH II in HEK293/rGnRHR cells. Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 6B:
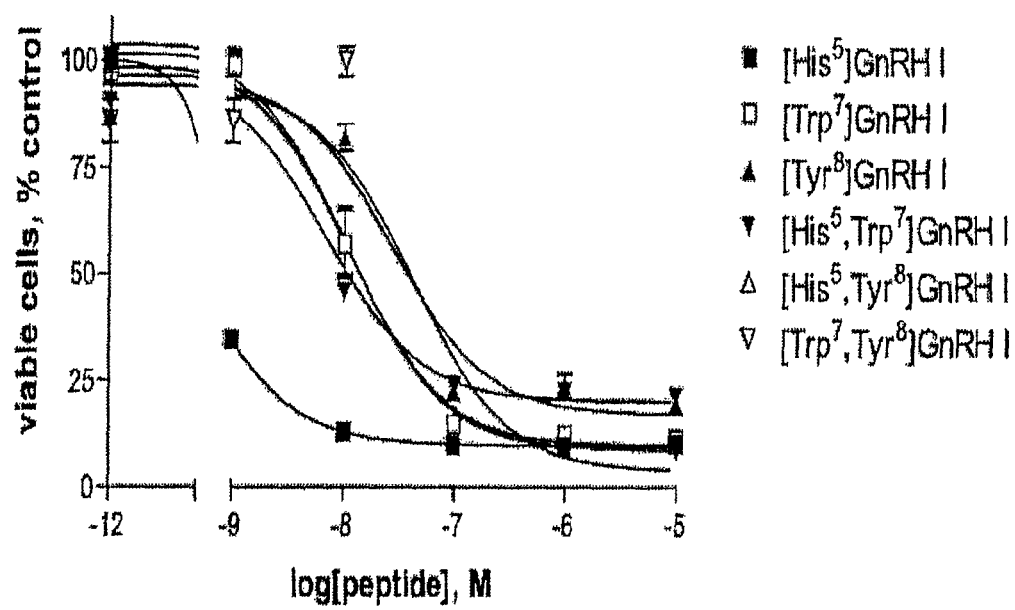

FIG. 6B. Antiproliferation curves for GnRH analogues in HEK293/rGnRHR cells. Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 7A:
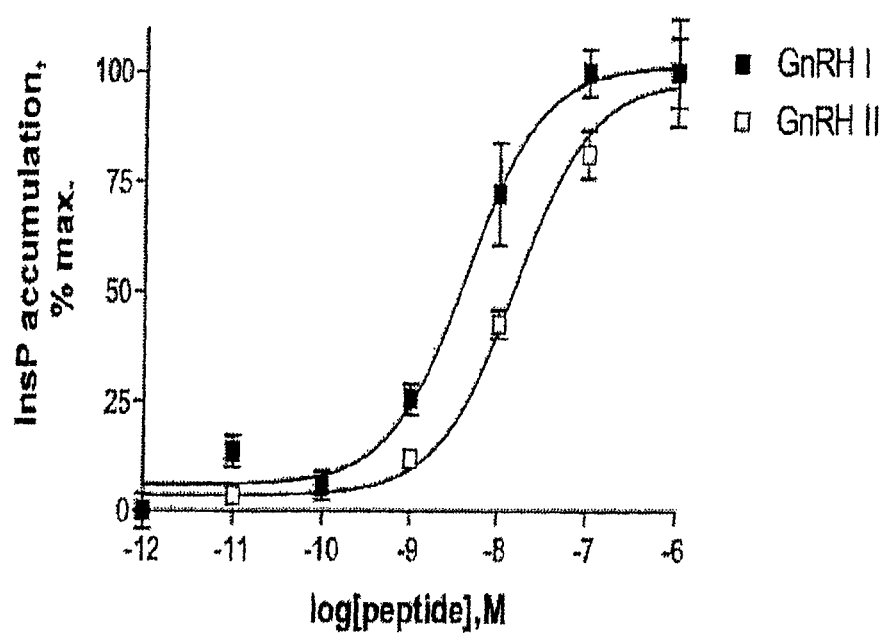

FIG. 7A. Total inositol phosphates accumulation curves for GnRH I and GnRH II in HEK293/hGnRHR cells. The curves represent one of at least three independent experiments in which each point represents the mean of sixtuplicate values with S.E.M displayed as error bars. Counts were normalised to the maximal response within each data set.

Figure 7B:
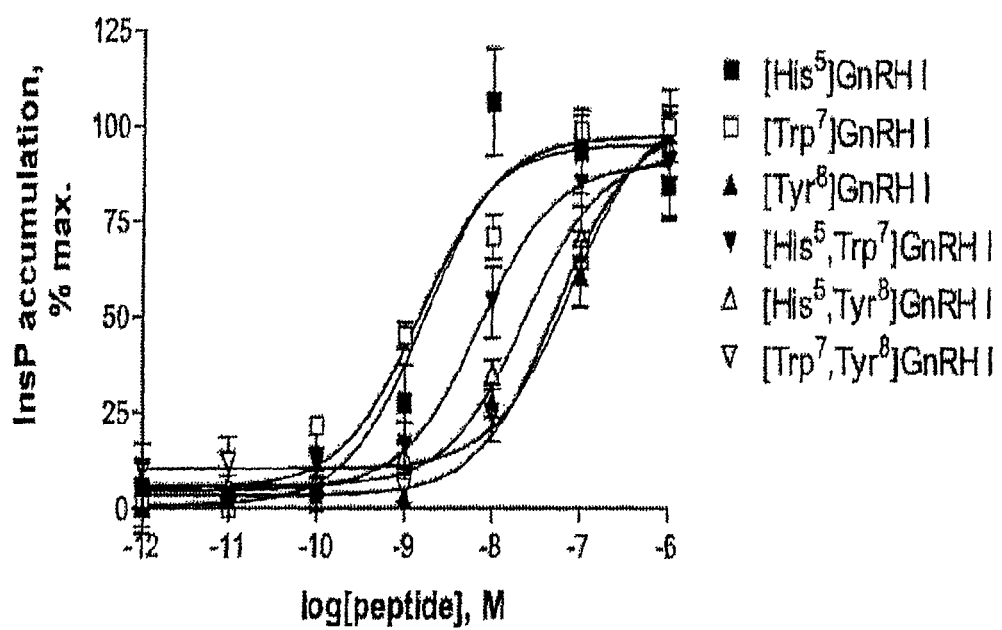

FIG. 7B. Total inositol phosphates accumulation curves for GnRH analogues in HEK293/hGnRHR cells. The curves represent one of at least three independent experiments in which each point represents the mean of sixtuplicate values with S.E.M displayed as error bars. Counts were normalised to the maximal response within each data set.

Figure 8A:
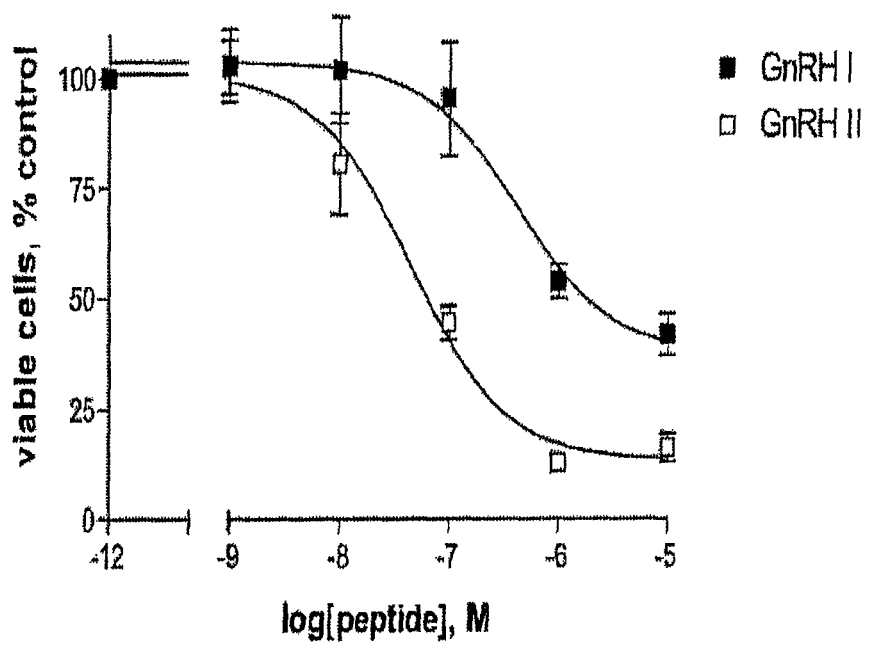

FIG. 8A. Antiproliferation curves for GnRH I and GnRH II in HEK293/hGnRHR cells. Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 8B:
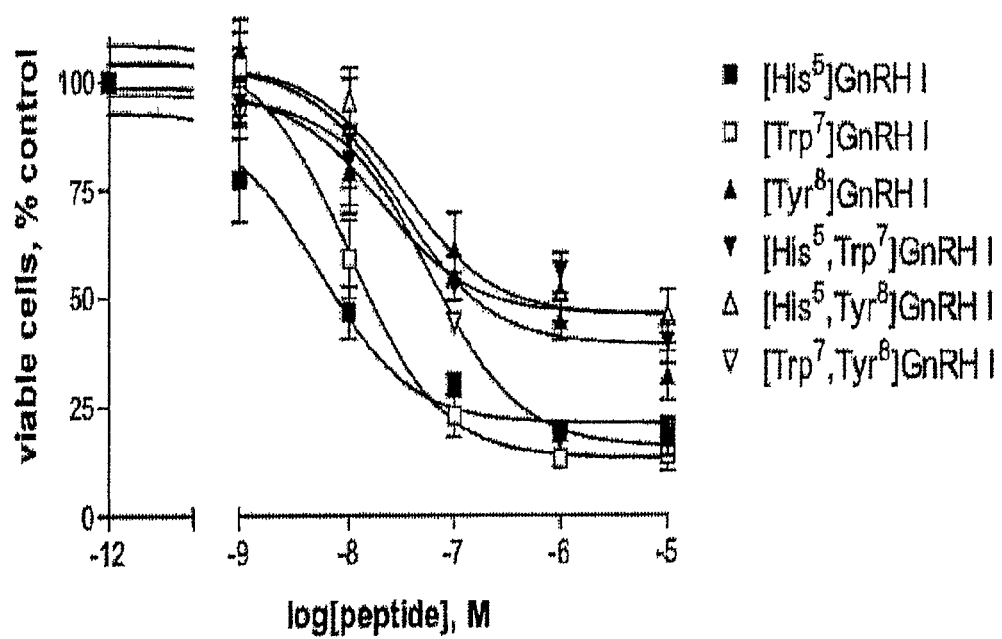

FIG. 8B. Antiproliferation curves for GnRH analogues in HEK293/hGnRHR cells. Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

FIG. 8C. IC50 values from competition binding assays and EC50 values for the accumulation of inositol phosphates (IP) and cell growth inhibition (AP) for natural and mutated GnRH peptides in HEK293/rGnRHR cells. The mean (nM) S.E.M. is shown, with the number of experiments indicated in brackets. * p<0.05,  p<0.01, * p<0.005. The GnRH receptor used in the rat GnRH receptor.

FIG. 8D. EC50 values for the accumulation of inositol phosphates and cell growth inhibition for natural and mutated GnRH peptides in HEK293/hGnRHR cells. The mean (nM)± S.E.M. is shown, with the number of experiments indicated in brackets. * p<0.05,  p<0.01, * p<0.005. The GnRH receptor used in the human GnRH receptor.

Figure 9:
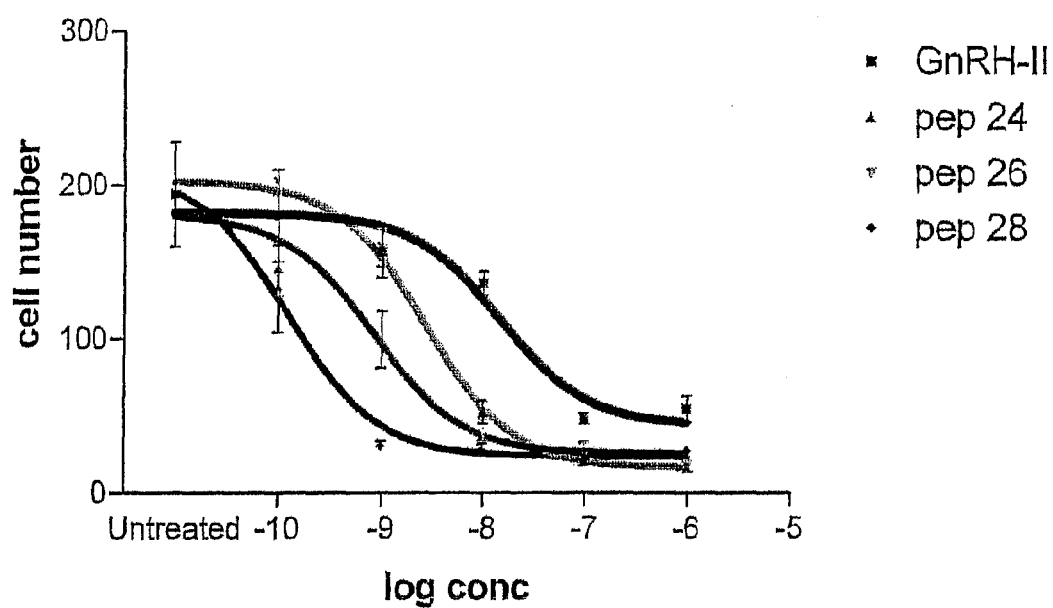

FIG. 9. Inhibition of proliferation of HEK293/hGnRH cells by peptides 24, 26 and 28 (as designated in FIG. 15). Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 10:
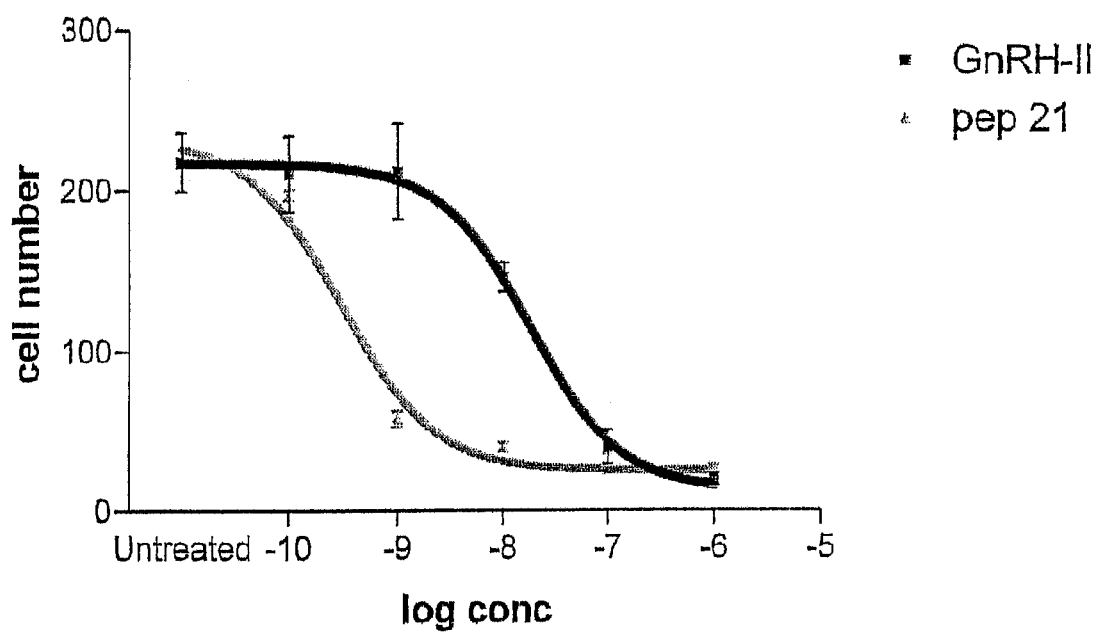

FIG. 10. Inhibition of proliferation of HEK293/hGnRH cells by peptide 21 (as designated in FIG. 15). Cells were continuously treated with the agonist for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 11:
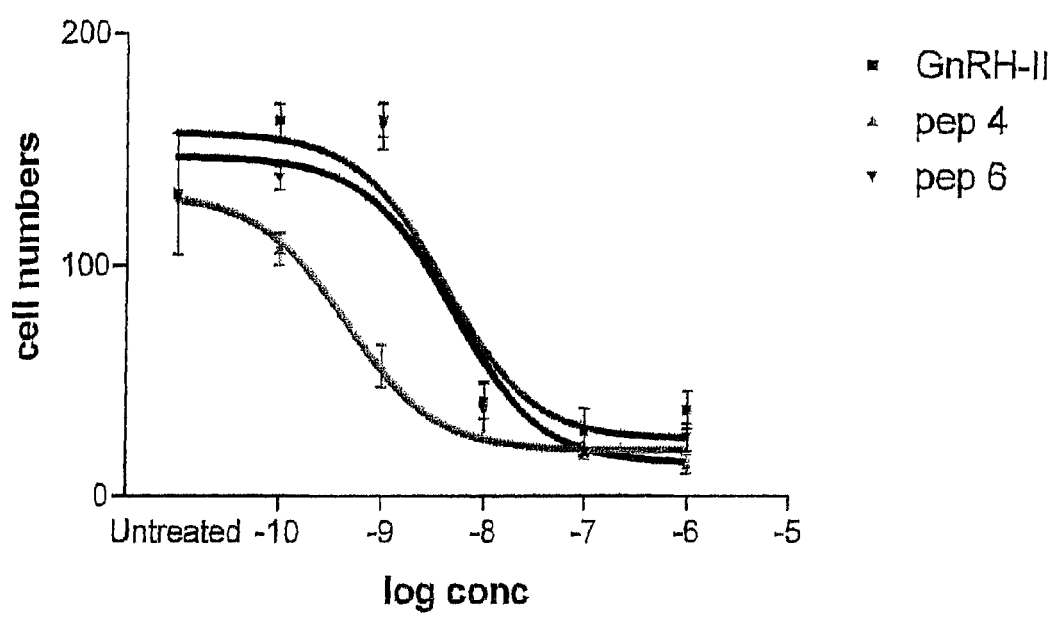

FIG. 11. Inhibition of proliferation of HEK293/hGnRH cells by peptides 4 and 6 (as designated in FIG. 15). Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 12:
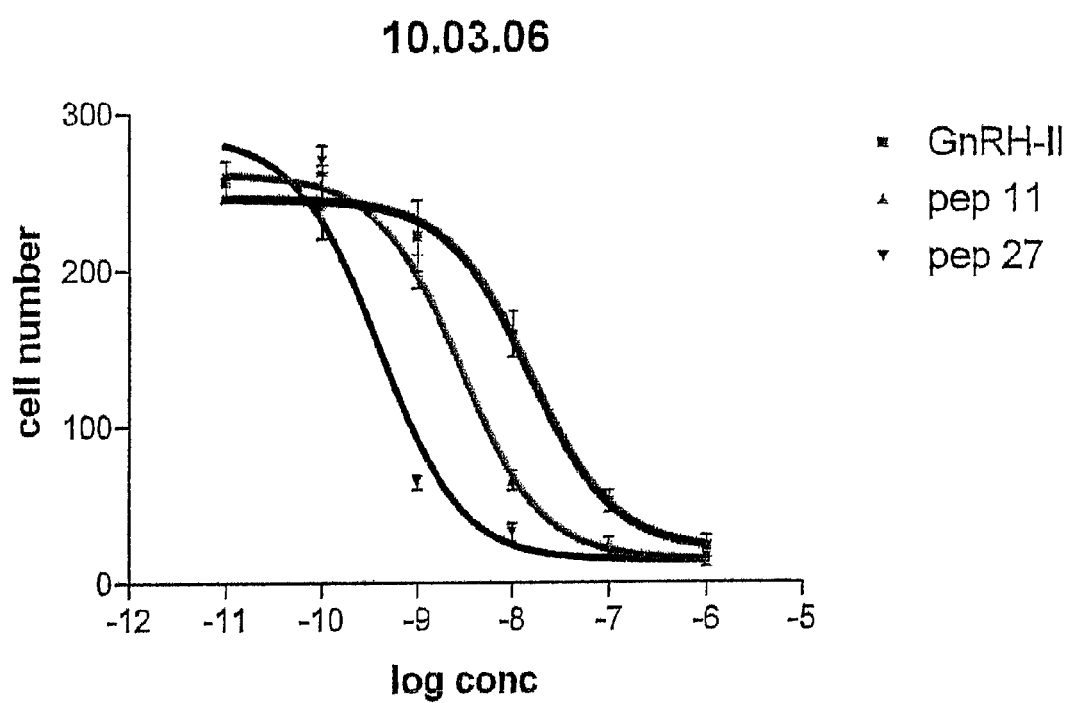

FIG. 12. Inhibition of proliferation of HEK293/hGnRH cells by peptides 11 and 27 (as designated in FIG. 15). Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 13:
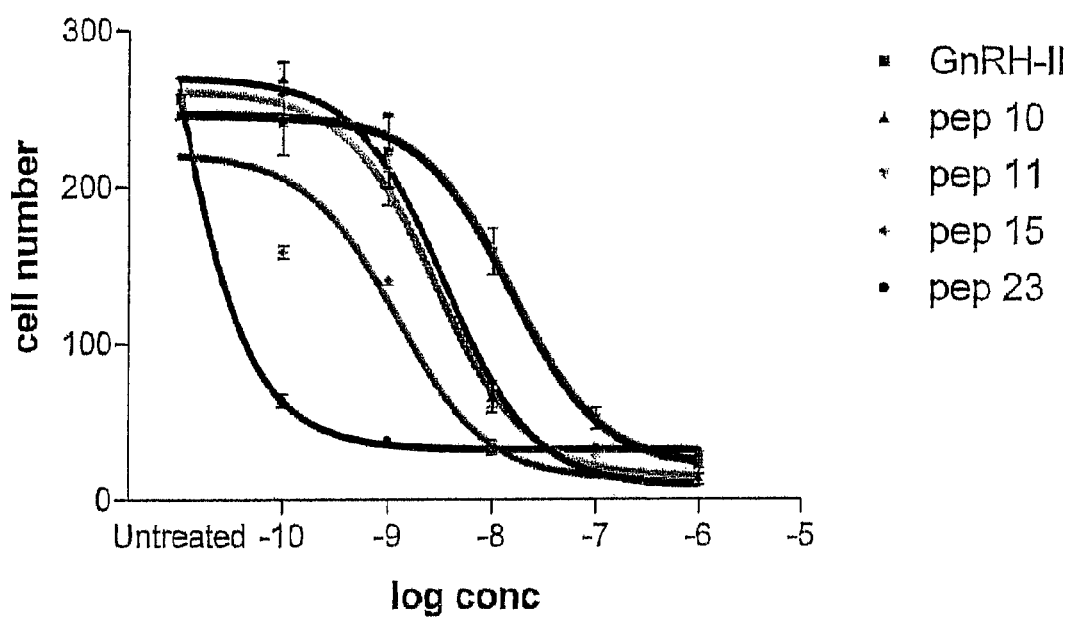

FIG. 13. Inhibition of proliferation of HEK293/hGnRH cells by peptides 10, 11, 15 and 23 (as designated in FIG. 15). Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

Figure 14:
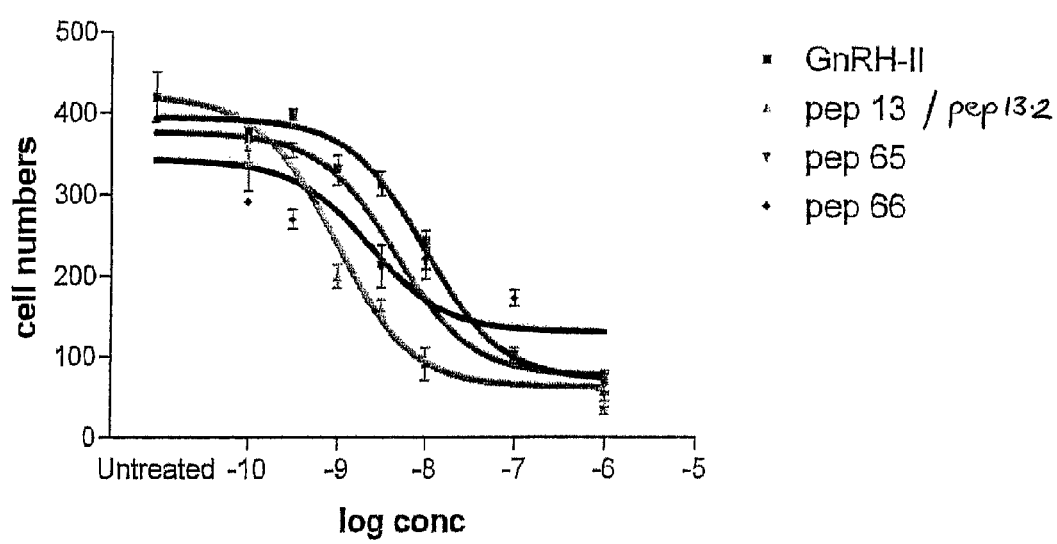

FIG. 14. Inhibition of proliferation of HEK293/hGnRH cells by peptides 13, 65 and 66 (as designated in FIG. 15). Cells were continuously treated with the agonists for 5 days and then viable cells were counted with a haemocytometer after Trypan blue incubation. The curves represent one of at least three independent experiments in which each point represents the mean of triplicate values with S.E.M displayed as error bars. Values were normalised to the number of cells that had been left untreated.

FIG. 15. Inhibition of cell number and inositol phosphate production in HEK293/hGnRH cells by GnRH analogues.

The listing or discussion of a prior-published document in this specification should not be taken as an acknowledgement that the document is part of the state of the art or is common general knowledge.

Several publications and patent documents are cited in this application in order to more fully describe the state of the art to which this invention pertains. The disclosure of each of these citations is incorporated herein by reference herein.

EXAMPLE 1

Experimental Data

Materials and Methods

Materials

GnRH I and GnRH II were purchased from Sigma-Aldrich Co. Ltd. (Poole, Dorset, UK). Modified GnRH analogues were obtained from Roger Roeske (University of Indiana, Indianapolis, USA). Anti-phosphorylated ERK1/2 and anti-ERK2 antisera were obtained from New England Biolabs (UK) Ltd. (NEB; Hitchin, Herts, UK). Anti-cleaved poly [ADPribose]polymerase (PARP) antibody (Asp214/Gly215; human specific) was from Cell Signalling Technology, Inc. (Beverly, Mass., USA). All secondary antibodies were from Sigma. The chemical inhibitors JNK inhibitor II, PD98059 (MEK inhibitor), SB203580 (p38 MAPK inhibitor), wortmannin (PI-3K inhibitor), herbimycin A (tyrosine kinase inhibitor), PP2 (Src inhibitor), AG1478 (EGFR inhibitor), U-73122 (PLC inhibitor), Ro-31-8220 (PKC inhibitor) and Gö6983 (PKC inhibitor) were purchased from Calbiochem (Calbiochem/Merck Biosciences Ltd.; Nottingham, East Midlands, UK), while PTX (Gi inhibitor) was from Biomol (Biomol International; Exeter, Devon, UK) and 2-APB (2-aminoethyl-diphenilborinate) (IP3-induced Ca2+ release inhibitor) was from Sigma.

Cell Culture

The stable HEK293 cell lines expressing different GnRH receptor constructs belong to the laboratory stock and have been used in other studies (e.g. Heding et al., 1998). Cells were maintained in Dulbecco's modified Eagles medium (DMEM) (Sigma) supplemented with 10% fetal bovine serum, 2% glutamine and 1% penicillin (10,000 units/ml)/streptomycin (10,000 µg/ml) at 37° C. in a humidified 5% CO2 atmosphere. Cell treatments were performed at 37° C. in serum-containing medium with varying molecule concentrations and time periods, as indicated in the figure legends. The concentrations of the chemical inhibitors used to study the mechanism of PARP cleavage were: 5 µM JNK inhibitor II, 20 µM PD98059, 20 µM SB203580, 25 nM wortmannin, 200 ng/ml PTX, 1 µM herbimycin A, 5 µM PP2, 10 µM AG1478, 5 µM U-73122, 100 nM Ro-31-8220, 1 µM Gö 6983 and 20 µM 2-APB.

Immunoblotting

After stimulation of cells growing on 6-well plates, cell monolayers were placed on ice, washed twice in ice-cod Dulbecco's phosphate buffered saline (DPBS), and lysed in a NP-40-based solubilisation buffer (5 mM HEPES, 0.25 M NaCl, 0.5% NP-40, 10% glycerol, 2 mM EDTA pH8.0, 1 mM PMSF, 0.01 mg/ml leupeptin, 1 mM Na2VO4). Solubilised lysates were clarified by centrifugation at 15,000 rpm for 15 min. A 50 µl-aliquot of clarified whole-cell lysate was mixed with an equal volume of 2× Laemmli sample buffer, resolved by SDS-polyacrylamide gel electrophoresis (SDS-PAGE) and transferred to a PVDF membrane (NEN Life Sciences/PerkinElmer Life and Analytical Sciences; Beaconsfield, Bucks, UK). These membranes were blocked in a 4% bovine serum albumin, 50 mM Tris-HCl, pH 7.0, 0.05% Tween-20 and 0.05% NP-40 blocking solution. Phosphorylation of ERK1/2 was detected with a 1:1,000 dilution of anti-phospho-specific ERK1/2 rabbit polyclonal antibody (NEB). Apoptosis was assessed by incubating the PVDF membranes with a 1:1,000 dilution of anticleaved PARP rabbit polyclonal antibody at 4° C. with gentle shaking overnight. The extent of these responses was normalised by subsequently applying antisera (1:1,000 dilution) against the unphosphorylated form of ERK2 (NEB) to primary antibody-stripped immunoblots. An alkaline phosphatase conjugated IgG (Sigma) was employed as a secondary antibody in all cases. Visualization of proteins was performed using enzyme-linked chemifluoresence (Amersham Biosciences Ltd.; St. Giles, Bucks, UK) and quantified using a Typhoon 9400 Phosphorimager.

Cell Viability and Number

For the first method, HEK293 cells expressing various GnRH receptor constructs were seeded into 12-well PLL-coated plates at 50,000 cells (in 1 ml)/well and cultured with continuous GnRH exposure for five days, adding fresh peptide every day. Trypan Blue-excluding cells were then counted with a haemocytometer. For the second method, cells were seeded into 96-well plates at 5,000 cells (in 100 µl)/well and treated exactly as described before. 10 µl WST-1 reagent (Roche Diagnostics Ltd.; Lewes, East Sussex, UK) was added directly to each well and, after 3 h at 37° C., absorbance was read at 450 nm (with a reference at 690 nm) against a background control as blank using a microplate ELISA reader.

Thymidine Incorporation Assay

Medium of cells growing on 24-well PLL-coated plates was removed and 0.5 µCi [3H]thymidine (Amersham) in complete fresh medium was added to each well. After an overnight incubation, the medium was removed, the cells washed three times with 1 ml PBS and left for 15 mM at room temperature in 0.5 ml 0.1 N NaOH. The extract was then transferred to a scintillation vial, 2 ml of Optiphase "HiSafe 3" cocktail (PerkinElmer) added and 3H counts measured in a liquid scintillation 1450 Wallac MicroBeta® TriLux counter.

Binding Assay

Specific binding of 80 pM [125I][His5,D-Trp6]GnRH I to HEK293 cells expressing the GnRH receptor was calculated as the difference between the amount of labeled GnRH I bound in the absence and presence of various unlabelled ligands. Cell monolayers growing on 12-well PLL-coated plates were incubated in binding buffer (10 mM HEPES, 1% BSA in DMEM) containing 80 µM radioligand (100,000 cpm) and 10-6-10-12 M unlabelled ligand. Equilibrium was reached after incubation for 4 h at 4° C. Cells were then lysed in 0.1 M NaOH and the radioactivity in the extract was measured in a 1261 Wallac MultiGamma counter.

Accumulation of Total Inositol Phosphates

HEK293 cells stably expressing the GnRH receptor growing on 12-well PLL-coated plates were pre-labelled with 1 µCi/ml myo-[H3]inositol (Amersham) in inositol-free DMEM (Sigma) for 48 h. On the day of the experiment, cells were washed with assay buffer (140 mM NaCl, 20 mM HEPES, 8 mM glucose, 4 mM KCl, 1 mM MgCl2, 1 mM CaCl2, 1 mg/ml BSA), pre-incubated with 10 mM LiCl (in assay buffer) for 30 min, and stimulated with different concentrations of the peptides (in the same buffer) for 1 h at 37° C. Incubations were terminated by removing the culture medium and lysing the cells in ice cold 10 mM formic acid for 30 min. Inositol phosphates were extracted by chromatography with an anion exchange resin (AG® 1-X8, Bio-Rad) using 1 M ammonium formate and 0.1 M formic acid. Liquid scintillant was added to the final eluate and [3H]inositol phosphates were measured in the β-counter.

Data Analysis

Bar graphs and curves were obtained using Prism 3.0 (GraphPad Software, Inc.: San Diego, Calif., USA). IC50 and EC50 values were determined by non-linear regression analysis. Curves were best-fitted to a one-site model. The figures shown represent one of at least three independent experiments for which each point represents the mean of triplicate values with the standard error of the mean (S.E.M.) displayed as error bars, unless otherwise stated. Values were normalised as specified in the figure legends.

Results

Lack of C-terminal Tail is a Receptor Requirement to Transduce Cell Growth Inhibition To the best of our knowledge, the ability to inhibit the growth of cells expressing its cognate receptor is a property only clearly described for GnRH, Since the type I GnRH receptor (GnRHR) is the only G protein-coupled receptor lacking an intracellular C-terminal tail, we hypothesized that the cell growth suppression ability of GnRH was conferred by this unique feature of the GnRHR. We compared the effect of GnRH I on the growth of four different HEK293 cell lines stably expressing the human GnRHR, the rat GnRHR, and two chimeric receptors comprising the human GnRHR with the tail of the catfish GnRHR and the rat GnRHR with the tail of the TRH receptor (TRHR), along with wild-type HEK293 cells. Cell growth was determined by counting the cells after five days of continuous treatment with GnRH I. Addition of the C-terminal tails inhibited the effect of GnRH I on the two cell lines expressing the chimeras (FIG. 1A). GnRH I did not inhibit the growth of HEK293 cells over-expressing the catfish GnRHR or the TRHR (data not shown). We were unable to detect growth suppression of wild-type HEK293 cells, which endogenously express adrenergic, LPA and endothelin receptors, treated with their corresponding agonists (data not shown). The expression of all receptors mentioned was confirmed by binding assays or western blotting (data not shown). We also ruled out the presence of type II GnRHR because the 135-18 peptide, which is a type I receptor antagonist but a type II receptor agonist, blocked the antiproliferative effect of GnRH I and did not induce accumulation of inositol phosphates or growth suppression in these cells.

ERK Desensitisation Profiles

Due to the absence of a C-terminal tail, the GnRHR does not rapidly desensitise, resulting in prolonged PLCβ activation (e.g. McArdle 2002). We decided to investigate if this lack of rapid desensitisation holds true for other responses that may be more pertinent for the antiproliferative/apoptotic properties of GnRH. HEK293 cells expressing the rat GnRHR or the rat GnRHR/TRHR chimera were treated with 100 nM GnRH I for different time periods and determined the activation of ERK by western blot. As shown in FIG. 1B, the activation of ERK is more sustained in the cells expressing the receptors lacking the C-terminal tail.

Concomitant DNA Synthesis Inhibition and Apoptosis Produce Cell Growth Suppression We investigated whether the growth suppression caused by GnRH on HEK293 cells expressing the rat receptor was due to an inhibition of cell proliferation or an induction of apoptosis. On the one hand, we used radioactive thymidine incorporation into the genome to track cell proliferation over a period of 96 h. Continuous treatment with both GnRH I and, more clearly, GnRH II (100 nM) reduced DNA replication, compared to untreated cells (FIG. 2A). On the other hand, we measured apoptosis by monitoring cleavage of poly[ADP-ribose]polymerase (PARP), a substrate of caspase 3. Using this output, GnRH II (100 nM)-induced apoptosis was definitely manifest as soon as 24 h after the first treatment, while GnRH I needed at least 48 h to induce PARP cleavage under the same conditions (FIG. 2B). The increase of cleaved PARP in the cytoplasm was proportional to the increase of cleaved PARP in the nucleus (data not shown), so we routinely only examined clarified whole-cell lysates for technical ease.

Molecular Mechanism of Apoptosis

Taking advantage of the relatively fast and strong signal obtained in the PARP assay in the HEK293/rGnRHR cell line, we explored the intracellular mechanism mediating this effect using a large panel of chemical inhibitors. The cells we cultured at sub-confluence and treated with 100 nM agonist in the absence or presence of inhibitors in complete medium for 48 h. Then, cells were lysed and a western blot with specific anti-cleaved PARP antibody was carried out as explained before. As shown in FIGS. 3A and 3B, five inhibitors blocked more than 50% of total agonist induced caspase 3 activation; namely PD98059 (17±6; 14±13), herbimycin A (9±1; 41±4), PP2 (20±4; 18±2), Gö 6983 (47±22; 35±18) and AG1478 (13±10; 18±11) (numbers in parenthesis are the mean±S.E.M. of the remaining GnRH I and GnRH II-induced PARP cleavage, respectively). The JNKII inhibitor also decreased the apoptosis induced by GnRH I and GnRH II, but to a lesser extent (84±29; 72±22). Incidentally, the results for a few inhibitors should be carefully interpreted because of cytotoxicity (SB203580 and 2-APB caused significant PARP cleavage by themselves) or great variability among individual assays (SB203580, PTX and wortmannin).

Structure-activity Relationship of Analogues with Respect to Cell Growth Inhibition Therefore, GnRH II appeared to be more efficient to induce antiproliferation and apoptosis of the same cell lines than GnRH I. The decapeptides GnRH I and GnRH II differ in three amino acids, thus GnRH II can be viewed as an analogue of GnRH I. We decided to study the structure-activity relationship of GnRH analogues in relation to their antiproliferative/apoptotic effect, establishing this report as the first of this kind. The three differing amino acids, His5, Trp7 and Tyr8, were incorporated individually or in pairs into the GnRH I sequence, resulting in six different analogues structurally intermediate between GnRH I and GnRH II.

Antiproliferation/apoptosis was estimated by determining cell number after five days of continuous exposure to the peptides. In parallel, this response was compared to the classical Gq coupled-PLCβ activation induced by GnRH peptides, as measured by the very well characterized inositol phosphates accumulation protocol. Both outputs were determined in two HEK293 cell lines; one expressing the rat receptor and the other expressing the human receptor. The human cell line was included in the study because this species may be clinically more relevant and the very low receptor expression may better reflect the in vivo tumoural state. In fact, due to poor binding, the precise affinity of the analogues on this cell line could not be determined.

The affinity of all analogues accurately correlated with their potency to stimulate inositol phosphates accumulation, but not with their potency to produce antiproliferation/apoptosis (FIGS. 4A-8D). To illustrate this, at the rat receptor, GnRH I was 4.7-fold more potent to activate PLCβ than GnRH II, but GnRH II was 13.0-fold more potent to induce cell death (FIGS. 5A, 6A, and 8C). Similarly, at the human receptor, GnRH I was 6.2-fold more potent to activate PLCβ than GnRH II, but GnRH II was 6.7-fold more potent to induce cell death (FIGS. 7A, 8A, and 8D). [His5]GnRH I displayed a higher affinity than GnRH I (FIGS. 4B and 8C), resulting in better potencies for the two responses studied (FIGS. 5B, 6B, 7B, 8B, 8C and 8D). Remarkably, this analogue is the most potent antiproliferative/apoptotic agent ever described. The introduction of Trp7 into GnRH I did not modify the affinity and PLCβ activation capacity of the native peptide (FIGS. 4B, 5B, 7B, 8C and 8D). However, [Trp7] GnRH I is 9.1-fold and 19.3-fold more potent than GnRH I to inhibit the growth of cells expressing the rat and human receptor, respectively (FIGS. 6B, 8B, 8C, and 8D). The substitution of Arg8 in GnRH I by Tyr8 was the single change that resulted in the most selective antiproliferative/apoptotic analogue. At the rat receptor, [Tyr8]GnRH I was 27.3-fold less potent to stimulate FLU but 4.2-fold more potent to inhibit cell growth, compared to GnRH I (FIGS. 5B, 6B, and 8C). Analogously, at the human receptor, this analogue was 23.7-fold less potent to stimulate PLCβ but 10.7-fold more potent to inhibit cell growth, again relative to the native peptide (FIGS. 7B, 8B, and 8D). Notably, although this analogue shows a very low affinity (FIGS. 4B and 8C), it is still more potent than GnRH I to produce cell death. The two double mutant peptides that incorporate His at position 5, namely [His5,Trp7]GnRH I and [His5,Tyr8]GnRH I, display phenotypes that can be roughly explained by the single substitutions. Thus, [His5,Trp7]GnRH I has similar affinity and PLCβ activation potency to GnRH I, but improved antiproliferative/apoptotic capacity (FIGS. 4B, 5B, 6B, 7B, 8B, 8C, and 8D). [His5,Tyr8]GnRH I shows features intermediate between GnRH I and [Tyr8]GnRH I (FIGS. 4B, 5B, 6B, 7B, 8B, 8C, and 8D). The loss of affinity due to the Tyr8 substitution and subsequent decreased potency to stimulate PLCβ, seems to be partly rescued by the introduction of His5, which leads to increased affinity in the single [His5]GnRH I analogue. As expected, [His5,Tyr8]GnRH I is more potent to inhibit cell growth than GnRH I (and [Tyr8]GnRH I). Finally, the features of [Trp7,Tyr8]GnRH I are almost identical to those of [Tyr8]GnRH I (FIGS. 4B, 5B, 6B, 7B, 8B, 8C, and 8D).

Effects of D-amino Acid Substitution in Position 6 of GnRH Analogues on Proliferation of HEK293/Human GnRH Receptor Cells.

A series of D-amino acid substitutions in position 6 was made in GnRH II and GnRH I/II chimeras to establish structures with high antiproliferative potency. This revealed analogues with a 10-fold increase in potency over GnRH II (for example, peptides 13, 15, 21, 23, 24, 27 and 28) and analogues with greater than 10-fold selectivity (for example, peptides 15, 24, 26 and 28).

Some analogues are particularly potent (such as peptides 21, 23 and 28). Some analogues (for example, peptides 4, 11 and 28) have preferential antiproliferative effects compared with inositol phosphate production.

Discussion

The mammalian GnRH receptor (GnRHR) is the only GPCR that does not possess an intracellular C-terminal tail (Millar et al., 2004). Here we show that this structural peculiarity confers the GnRH receptor a unique property: the ability to mediate cell growth suppression. The same native and chimeric receptors used in the present study have been previously used in the past to investigate their desensitisation and internalisation profiles in a number of cellular contexts, including HEK293 and gonadotrope cell lines (Blomenrohr et al., 1999; Heding et al., 1998; Heding et al., 2000; Hislop et al., 2001; Hislop et al., 2000; Lin et al., 1998; Pawson et al., 1998; Vrecl et al., 1998; Willars et al., 1999). These studies demonstrate that non-mammalian tails contain phospho-acceptor sites, which is linked to increased rates of desensitisation to activate Gq/PLCβ and receptor internalisation after repeated GnRH binding. Tailed receptors are also reported to be more highly expressed at the plasma membrane (Heding et al., 1998; Lin et al., 1998). Although Hislop et al. (2001), record that the human (tail-less) and the Xenopus (tailed) receptors show similar desensitisation patterns with respect to ERK activation, we have observed that addition of a tail to the rat receptor also increased the desensitisation rate of this response in HEK293 cells. This may insinuate that the absence of a C-terminal tail may bestow on the mammalian GnRH receptor other functional characteristics not previously recognised.

In addition, we have shown that HEK293 cell growth inhibition exerted by GnRH I is the result of the combination of DNA synthesis inhibition and apoptosis induction. This is in line with previous reports of GnRH action on these and other cell types (Kim et al., 2004a; Miles et al., 2004; Maudsley et al., 2004; Limonta et al., 2003 Grundker, 2002). Furthermore, using a large series of chemical inhibitors, we have demonstrated that GnRH I and GnRH II-induced apoptosis in HEK293 cells requires Src, the EGF receptor, ERK and, possibly, PKC. While the implication of the first three elements is clear, the role of PKC is more arguable. First, the extent of the effect of the PKC inhibitors upon GnRH-stimulated apoptosis (~40% by Gö 6983) is not so dramatic as that caused by the others, indicating that PKC may not be part of the principal signalling cascade leading to caspase 3 activation. Second, the results obtained with the two PKC inhibitors are not coincident. G Gö 6983 was clearly more efficient than Ro-31-8220 to decrease the GnRH effect. This can be explained because the two molecules block different PKC isoforms or because the concentrations of Ro-31-8220 used in this assay were sub-optimal.

Finding that EGFR and ERK mediate GnRH-induced apoptosis was unexpected, since activation of these molecules is generally associated with the transduction of mitogenic signals and cell proliferation. Indeed, the interference of GnRH I with EGF and IGF signalling and subsequent down-regulation of ERK activity has been shown in some cancer cell lines (Limonta et al., 2003). However, an increasing number of recent reports also describe ERK as a component of the apoptotic response (e.g. Song et al., 2005). Of special relevance for the GnRH system, inhibition of ERK has been shown to block GnRH I-induced cell cycle arrest in the Caov-3 human ovarian cancer cell line and GnRH II-induced Elk-1 phosphorylation in the OVCAR3 human ovarian cancer cell line (Kimura et al., 1999; Kim et al., 2004b). ERK phosphorylates many membrane, cytoplasmic and nuclear substrates depending on its cellular location and time courses of activation (Luttrell, 2003). In HEK293/rGnRHR treated with a high dose of GnRH for a long time (requirements to induce apoptosis), we may find, predominantly, the prolonged activation of a cytoplasmic pool of ERK that eventually stimulates caspase 3 activity. This idea is indirectly supported by the observation that Ro has no effect on GnRH-induced apoptosis, since Ro-31-8220 has been shown to inhibit nuclear substrates of ERK that mediate its transcriptional effects (RSK and MSK) (Davies et al., 2000).

Farshori et al. (2003) report that ERK activation in HEK293/mouse GnRHR is mediated by PKCδ and Pyk2, but exclude Src and EGF receptor involvement. Although apparently contrary to our results, this may not be the case, since we have demonstrated a role for Src, EGFR and ERK in GnRH-induced apoptosis but do not show that they necessarily belong to the same signalling pathway converging at ERK. In addition, the experimental conditions are radically different; i.e. 10 min in serum-free medium (Farshori's ERK activation assay) v. 48 h in complete medium (our PARP assay). EGFR is activated by GnRH in other cellular contexts (Grosse et al., 2000; Kraus et al., 2004).

The broad tyrosine kinase inhibitor herbimycin A and the specific Src family tyrosine kinase inhibitor PP2 suggested a role for this group of kinases in GnRH-stimulated apoptosis in HEK293 cells. Src participates in ERK and JNK activation by GnRH in pituitary and COS-7 cells (e.g. Grosse et al., 2000; Kraus et al., 2004), and it has been shown to mediate JNK activation leading to GnRH-induced growth inhibition of the DU-145 prostatic cancer cell line. Besides, we have recently demonstrated in the HEK293/rGnRHR cell line that GnRH I activates c-Src, which then binds the lipid kinase DGKζ (Davidson et al., 2004). In this study we do not resolve if Src is activated up-stream or down-stream of the EGF receptor. If up-stream, Src could be activated by different effectors, including PKC, the βγ or αi G protein subunits or even by direct interaction with the GPCR.

Unlike in other cell types (e.g. Maudsley et al., 2004), we were unable to clearly demonstrate that Gαi mediates antiproliferation of HEK293/rGnRHR cells. In addition to PTX not having any effect on GnRH-induced caspase 3 activation, we did not detect FSK-stimulated cAMP inhibition by GnRH I or GnRH II or Gi-coupling to the receptor by a scintillation proximity assay (SPA) in these cells (Coetsee et al., unpublished results). This was also the case of JNK or p38 MAPK mediation in GnRH-stimulated apoptosis, although toxicity of SB203580 might have masked any p38 MAPK involvement. However, we agree with the general view that PLC, representing the classical Gq-initiated pituitary signalling pathway, is not a relevant component of the apoptotic cascade. This does not contradict partial PKC involvement, since there are rare PKC isoforms that are DAG and Ca2+ independent (Naor et al., 1998). Taking all together, it is plausible to postulate that the apoptotic effects of GnRH I and GnRH II in HEK293 cells may not be mediated by heterotrimeric proteins, but other receptor interacting molecules such as Src, β-arrestin or small G proteins.

The development of more potent and, very importantly, more selective agents for cancer therapy is crucial. Until now, research on the structure-activity relationship (SAR) in the GnRH system had focused on the ability of ligands to modulate Gq/PLCβ. Since we now know that this is not the effector pathway leading to antiproliferation, it is necessary to monitor other outputs when studying SAR of ligands in relation to cell growth inhibition. In this report we not only study the binding affinity and potency to induce accumulation of phosphoinositides by a series of analogues, but also study in detail for the first time the ligand structural requirements to produce cell growth suppression. Towards this aim, we used HEK293 cells expressing either the rat or the human GnRHR, the latter possessing very low receptor numbers.

Mammalian GnRH I and GnRH II can be divided in three structural regions (Millar et al., 2004; Sealfon et al., 1997). The N-terminal Glu1-His2-Trp3-Ser4 and C-terminal Pro9-Gly10 sequences have been conserved over 500 million years. While both regions contribute to receptor binding, only the N-terminal amino acids are also critical for receptor activation leading to Gq coupling. The middle domain is much less conserved among species and among the various GnRH peptides present in the same species. This region corresponds to Tyr5-Gly6-Leu7-Arg8 in GnRH I and to His5-Gly6-Leu7-Tyr8 in GnRH II. The high-affinity interaction of GnRH with type I mammalian GnRH receptors requires a β-II' turn conformation of the ligand involving these residues (Momany, 1976 and references in Millar et al., 2004). The proposed interactions that confer this conformation are those between Ser4 and Arg8, Glu1 and Gly10 and/or Arg8 with His 2 and Tyr5 (Millar et al., 2004). Arg8 has also been shown to interact with the conserved Asp302 in the third extracellular loop of the mammalian GnRH receptor, which induces or selects the β-II'turn conformation (Flanagan et al., 1994; Fromme et al., 2001). Arg8 does not seem to be directly involved in receptor activation resulting in Gq stimulation, but may play an indirect role by virtue of its binding to Asp302, since this residue has been postulated to establish intramolecular contacts with the Glu90-Asn102-Lys121-activation triad (Millar et al., 2004). There is evidence to suggest that GnRH II is preconfigured in the β-II' turn conformation, which accounts for its relative high affinity for, all GnRH receptors (Pfleger et al., 2002).

The affinity of all peptides in our study accord with previous reports using rat anterior pituitary membranes or COS-7 and HEK293 cells transiently expressing the rat or human receptors (Miles et al., 2004; Millar et al., 2004; Pfleger et al., 2002). Compared to GnRH I, GnRH II displayed a lower potency to induce inositol phosphates accumulation but a much higher potency to inhibit the growth of the same cells. Substitution of Tyr5 by His5 in GnRH I resulted in increased affinity, which correlated with a higher potency in the two responses studied. [His5]GnRH I is the most potent cell growth suppressor in the GnRH system ever described. Replacing Leu7 by Trp7 led to an analogue with same potency to stimulate PLCβ but higher potency to induce cell growth inhibition, compared with GnRH I. Substitution of Arg8 by Tyr8 produced the most selective antiproliferative/apoptotic agent. Relative to GnRH I, it exhibited a much lower binding affinity and potency to activate PLCβ. However, [Tyr8]GnRH I was 4-11-fold more potent to suppress cell growth. Other mutant peptides exhibited functional parameters expected from their intermediate structural characteristics between GnRH I and GnRH II.

Notably, this study supports the ligand-induced selective signalling (LISS) concept previously proposed for the GnRH receptor system by our group (Maudsley et al., 2004). This can be exemplified by GnRH I and GnRH II, which show inverted potency ratios for two responses (PLCβ activation and cell growth inhibition). In a system with a single type of receptors, two agonists with the same affinity and same signal strength that exhibit a reversal in the rank of relative potencies may selectively stabilize distinct receptor active states, each primarily responsible for the different responses observed.

In summary, we have provided new insights into the receptor pharmacology and intracellular mechanism involved in GnRH-induced cell growth inhibition and have inaugurated the path to the rational design of new analogues for GnRH-based cancer therapeutics.

EXAMPLE 2

Exemplary Pharmaceutical Formulations

Whilst it is possible for a agent of the invention to be administered alone, it is preferable to present it as a pharmaceutical formulation, together with one or more acceptable carriers. The carrier(s) must be "acceptable" in the sense of being compatible with the agent of the invention and not deleterious to the recipients thereof. Typically, the carriers will be water or saline which will be sterile and pyrogen-free.

The following examples illustrate medicaments and pharmaceutical compositions according to the invention in which the active ingredient is an agent of the invention.

Preferably, the agent of the invention is provided in an amount from 10 μg to 500 mg. It will be appreciated that the following exemplary medicaments and pharmaceutical compositions may be prepared containing an amount of the agent of the invention from 10 μg to 500 mg. For example, the agent of the invention may be present in a $10^{th}$ or $100^{th}$ or $200^{th}$ or $500^{th}$ of the amount shown in the following exemplary medicaments and pharmaceutical compositions with the amounts of the remaining ingredients changed accordingly.

Example A: Tablet

| Active ingredient | 1 mg |
| Lactose | 200 mg |
| Starch | 50 mg |
| Polyvinylpyrrolidone | 5 mg |
| Magnesium stearate | 4 mg |

Tablets are prepared from the foregoing ingredients by wet granulation followed by compression.

Example B: Ophthalmic Solution

| Active ingredient | 1 mg |
| Sodium chloride, analytical grade | 0.9 g |
| Thiomersal | 0.001 g |
| Purified water to | 100 ml |
| pH adjusted to | 7.5 |

Example C: Tablet Formulations

The following formulations A and B are prepared by wet granulation of the ingredients with a solution of povidone, followed by addition of magnesium stearate and compression.

Formulation A

| | mg/tablet | mg/tablet |
|---|---|---|
| (a) Active ingredient | 1 | 1 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
| | 251 | 51 |

Formulation B

| | mg/tablet | mg/tablet |
|---|---|---|
| (a) Active ingredient | 1 | 1 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
| | 251 | 51 |

Formulation C

| | mg/tablet |
|---|---|
| Active ingredient | 1 |
| Lactose | 200 |
| Starch | 50 |
| Povidone | 5 |
| Magnesium stearate | 4 |
| | 260 |

The following formulations, D and E, are prepared by direct compression of the admixed ingredients. The lactose used in formulation E is of the direction compression type.

Formulation D

|  | mg/capsule |
|---|---|
| Active Ingredient | 1 |
| Pregelatinised Starch NF15 | 150 |
|  | 151 |

Formulation E

|  | mg/capsule |
|---|---|
| Active Ingredient | 1 |
| Lactose | 150 |
| Avicel ® | 100 |
|  | 251 |

Formulation F (Controlled Release Formulation)

The formulation is prepared by wet granulation of the ingredients (below) with a solution of povidone followed by the addition of magnesium stearate and compression.

|  |  | mg/tablet |
|---|---|---|
| (a) | Active Ingredient | 1 |
| (b) | Hydroxypropylmethylcellulose (Methocel K4M Premium) ® | 112 |
| (c) | Lactose B.P. | 53 |
| (d) | Povidone B.P.C. | 28 |
| (e) | Magnesium Stearate | 7 |
|  |  | 201 |

Drug release takes place over a period of about 6-8 hours and was complete after 12 hours.

Example D: Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

|  |  | mg/capsule |
|---|---|---|
| (a) | Active ingredient | 1 |
| (b) | Lactose B.P. | 143 |
| (c) | Sodium Starch Glycolate | 25 |
| (d) | Magnesium Stearate | 2 |
|  |  | 171 |

Formulation C

|  |  | mg/capsule |
|---|---|---|
| (a) | Active ingredient | 1 |
| (b) | Macrogol 4000 BP | 350 |
|  |  | 351 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 1 |
| Lecithin | 100 |
| Arachis Oil | 100 |
|  | 201 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  |  | mg/capsule |
|---|---|---|
| (a) | Active ingredient | 1 |
| (b) | Microcrystalline Cellulose | 125 |
| (c) | Lactose BP | 125 |
| (d) | Ethyl Cellulose | 13 |
|  |  | 264 |

Example E: Injectable Formulation

| Active ingredient | 1 mg |
|---|---|
| Sterile, pyrogen free phosphate buffer (pH7.0) to | 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F: Intramuscular Injection

| Active ingredient | 1 mg |
|---|---|
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G: Syrup Suspension

| Active ingredient | 1 mg |
|---|---|
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H: Suppository

|  | mg/suppository |
|---|---|
| Active ingredient (63 μm)* | 1 |
| Hard Fat, BP (Witepsol H15-Dynamit Nobel) | 1770 |
|  | 1771 |

*The active ingredient is used as a powder wherein at least 90% of the particles are of 63 μm diameter or less.

One fifth of the Witepsol H15 is melted in a steam-jacketed pan at 45° C. maximum.

The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I: Pessaries

|  | mg/pessary |
|---|---|
| Active ingredient | 1 |
| Anhydrate Dextrose | 380 |
| Potato Starch | 363 |
| Magnesium Stearate | 7 |
|  | 751 |

The above ingredients are mixed directly and pessaries prepared by direct compression of the resulting mixture.

The agents of the invention may also be formulated as for Zoladex, Leuprolide, Teverelix, Abarelix, Ganarelix, Goserelin etc.

EXAMPLE 3

Treatment of a Proliferative Disorder Using an Agent of the Invention

A patient with prostatic cancer who has not responded to anti-androgen therapy is administered 1 mg of an agent of the invention per day intramuscularly according to the methods of the invention.

REFERENCES

Blomenrohr, M., Heding, A., Sellar, R., Leurs, R., Bogerd, J., Eidne, K. A. and Willars, G. B. (1999) Pivotal role for the cytoplasmic carboxyl-terminal tail of a nonmammalian gonadotropin-releasing hormone receptor in cell surface expression, ligand binding, and receptor phosphorylation and internalization. *Mol Pharmacol*, 56, 1229-1237.

Heding, A., Vrecl, M., Bogerd, J., McGregor, A., Sellar, R., Taylor, P. L. and Eidne, K. A. (1998) Gonadotropin-releasing hormone receptors with intracellular carboxyl-terminal tails undergo acute desensitization of total inositol phosphate production and exhibit accelerated internalization kinetics. *J Biol Chem*, 273, 11472-11477.

Heding, A., Vrecl, M., Hanyaloglu, A. C., Sellar, R., Taylor, P. L. and Eidne, K. A. (2000) The rat gonadotropin-releasing hormone receptor internalizes via a beta-arrestinindependent, but dynamin-dependent, pathway: addition of a carboxyl-terminal tail confers beta-arrestin dependency. *Endocrinology*, 141, 299-306.

Hislop, J. N., Everest, H. M., Flynn, A., Harding, T., Uney, J. B., Troskie, B. E., Millar, R. P. and McArdle, C. A. (2001) Differential internalization of mammalian and non-mammalian gonadotropin-releasing hormone receptors. Uncoupling of dynamin-dependent internalization from mitogen-activated protein kinase signaling. *J Biol Chem*, 276, 39685-39694.

Hislop, J. N., Madziva, M. T., Everest, H. M., Harding, T., Uney, J. B., Willars, G. B., Millar, R. P., Troskie, B. E., Davidson, J. S, and McArdle, C. A. (2000) Desensitization and internalization of human and xenopus gonadotropin-releasing hormone receptors expressed in alphaT4 pituitary cells using recombinant adenovirus. *Endocrinology*, 141, 4564-4575.

Lin, X., Janovick, J. A., Brothers, S., Blomenrohr, M., Bogerd, J. and Conn, P. M. (1998) Addition of catfish gonadotropin-releasing hormone (GnRH) receptor intracellular carboxyl-terminal tail to rat GnRH receptor alters receptor expression and regulation. *Mol Endocrinol*, 12, 161-171.

Millar, R. P., Lu, Z. L., Pawson, A. J., Flanagan, C. A., Morgan, K. and Maudsley, S. R. (2004) Gonadotropin-releasing hormone receptors. *Endocr Rev*, 25, 235-275, Pawson, A. J., Katz, A., Sun, Y. M., Lopes, J., Illing, N., Millar, R. P. and Davidson, J. S. (1998) Contrasting internalization kinetics of human and chicken gonadotropin-releasing hormone receptors mediated by C-terminal tail. *J Endocrinol*, 156, R9-12.

Vrecl, M., Anderson, L., Hanyaloglu, A., McGregor, A. M., Groarke, A. D., Milligan, G., Taylor, P. L. and Eidne, K. A. (1998) Agonist-induced endocytosis and recycling of the gonadotropin-releasing hormone receptor: effect of beta-arrestin on internalization kinetics. *Mol Endocrinol*, 12, 1818-1829.

Willars, G. B., Heding, A., Vrecl, M., Sellar, R., Blomenrohr, M., Nahorski, S. R. and Eidne, K. A. (1999) Lack of a C-terminal tail in the mammalian gonadotropin-releasing hormone receptor confers resistance to agonist-dependent phosphorylation and rapid desensitization. *J Biol Chem*, 274, 30146-30153.

Flanagan, C. A., Becker, II, Davidson, J. S., Wakefield, I. K., Zhou, W., Sealfon, S. C. and Millar, R. P. (1994) Glutamate 301 of the mouse gonadotropin-releasing hormone receptor confers specificity for arginine 8 of mammalian gonadotropin-releasing hormone. *J Biol Chem*, 269, 22636-22641.

Fromme, B. J., Katz, A. A., Roeske, R. W., Millar, R. P. and Flanagan, C. A. (2001) Role of aspartate7.32(302) of the human gonadotropin-releasing hormone receptor in stabilizing a high-affinity ligand conformation. *Mol Pharmacol*, 60, 1280-1287.

Maudsley, S., Davidson, L., Pawson, A. J., Chan, R., L Gópez de Maturana, R. and Millar, R. P. (2004) Gonadotropin-releasing hormone (GnRH) antagonists promote proapoptotic signaling in peripheral reproductive tumor cells by activating a Galphai-coupling state of the type I GnRH receptor. *Cancer Res*, 64, 7533-7544.

Miles, L. E., Hanyaloglu, A. C., Dromey, J. R., Pfleger, K. D. and Eidne, K. A. (2004) Gonadotropin-releasing hormone receptor-mediated growth suppression of immortalized LbetaT2 gonadotrope and stable HEK293 cell lines. *Endocrinology*, 145, 194-204.

Millar, R. P. and Pawson A. J. (2004) Outside-in and inside-out signaling: the new concept that selectivity of ligand binding at the gonadotropin-releasing hormone receptor is modulated by the intracellular environment. *Endocrinology*, 145,3590-359.3

Millar, R. P., Flanagan, C. A., Milton, R. C. and King, J. A. (1989) Chimeric analogues of vertebrate gonadotropin-releasing hormones comprising substitutions of the variant amino acids in positions 5, 7, and 8. Characterization of requirements for receptor binding and gonadotropin release in mammalian and avian pituitary gonadotropes. *J. Biol Chem*, 264, 21007-21013.

Millar, R. P., Lu, Z. L., Pawson, A. J., Flanagan, C. A., Morgan, K. and Maudsley, S. R. (2004) Gonadotropin-releasing hormone receptors. *Endocr Rev*, 25, 235-275.

Pfleger, K. D., Bogerd, J. and Millar, R. P. (2002) Conformational constraint of mammalian, chicken, and salmon GnRHs, but not GnRH II, enhances binding at mammalian and nonmammalian receptors: evidence for preconfiguration of GnRH II. *Mol Endocrinol*, 16, 2155-2162.

Sealfon, S. C., Weinstein, H. and Millar, R. P. (1997) Molecular mechanisms of ligand interaction with the gonadotropin-releasing hormone receptor. *Endocr Rev*, 18, 180-205.

Grundker, C., Gunthert, A. R., Westphalen, S. and Emons, G. (2002) Biology of the gonadotropin-releasing hormone system in gynecological cancers. *Eur J Endocrinol*, 146, 1-14.

Grundker, C., Schlotawa, L., Viereck, V., Eicke, N., Horst, A., Kairies, B. and Emons, G. (2004) Antiproliferative effects of the GnRH antagonist cetrorelix and of GnRH-II on human endometrial and ovarian cancer cells are not mediated through the GnRH type I receptor. *Eur J Endocrinol*, 151, 141-149.

Heding, A., Vrecl, M., Bogerd, J., McGregor, A., Sellar, R., Taylor, P. L. and Eidne, K. A. (1998) Gonadotropin-releasing hormone receptors with intracellular carboxyl-terminal tails undergo acute desensitization of total inositol phosphate production and exhibit accelerated internalization kinetics. *J Biol. Chem.*, 273, 11472-11477.

Limonta, P., Moretti, R. M., Marelli, M. M. and Motta, M. (2003) The biology of gonadotropin hormone-releasing hormone: role in the control of tumor growth and progression in humans. *Front Neuroendocrinol*, 24, 279-295.

Maudsley, S., Davidson, L., Pawson, A. J., Chan, R., López de Maturana, R. and Millar, R. P. (2004) Gonadotropin-releasing hormone (GnRH) antagonists promote proapoptotic signaling in peripheral reproductive tumor cells by activating a Galphai-coupling state of the type I GnRH receptor. *Cancer Res*, 64, 7533-7544.

Millar, R. P., Lu, Z. L., Pawson, A. J., Flanagan, C. A., Morgan, K. and Maudsley, S. R. (2004) Gonadotropin-releasing hormone receptors. *Endocr Rev*, 25, 235-275.

Enomoto, M., Endo, D., Kawashima, S. and Park, M. K. (2004) Human type II GnRH receptor mediates effects of GnRH on cell proliferation. *Zoolog Sci*, 21, 763-770.

Grundker, C., Gunthert, A. R., Westphalen, S. and Emons, G. (2002) Biology of the gonadotropin-releasing hormone system in gynecological cancers. *Eur J Endocrinol*, 146, 1-14.

Grundker, C., Schlotawa, L., Viereck, V., Eicke, N., Horst, A., Kairies, B. and Emons, G. (2004) Antiproliferative effects of the GnRH antagonist cetrorelix and of GnRH-II on human endometrial and ovarian cancer cells are not mediated through the GnRH type I receptor. *Eur J Endocrinol*, 151, 141-149.

Kaiser, U. B., Conn, P. M. and Chin, W. W. (1997) Studies of gonadotropin-releasing hormone (GnRH) action using GnRH receptor-expressing pituitary cell lines. *Endocr Rev*, 18, 46-70.

Limonta, P., Moretti, R. M., Marelli, M. M. and Motta, M. (2003) The biology of gonadotropin hormone-releasing hormone: role in the control of tumor growth and progression in humans. *Front Neuroendocrinol*, 24, 279-295.

Millar, R. P., Lu, Z. L., Pawson, A. J., Flanagan, C. A., Morgan, K. and Maudsley, S. R. (2004) Gonadotropin-releasing hormone receptors. *Endocr Rev*, 25, 235-275.

Morgan, K., Conklin, D., Pawson, A. J., Sellar, R., Ott, T. R. and Millar, R. P. (2003) A transcriptionally active human type II gonadotropin-releasing hormone receptor gene homolog overlaps two genes in the antisense orientation on chromosome 1q.12. *Endocrinology*, 144, 423-436.

Neill, J. D., Musgrove, L. C. and Duck, L. W. (2004) Newly recognized GnRH receptors: function and relative role. *Trends Endocrinol Metab*, 15, 383-392.

Chen, A., Kaganovsky, E., Rahimipour, S., Ben-Aroya, N., Okon, E. and Koch, Y. (2002) Two forms of gonadotropin-releasing hormone (GnRH) are expressed in human breast tissue and overexpressed in breast cancer: a putative mechanism for the antiproliferative effect of GnRH by down-regulation of acidic ribosomal phosphoproteins P1 and P2. *Cancer Res*, 62, 1036-1044.

Davies, S. P., Reddy, H., Caivano, M. and Cohen, P. (2000) Specificity and mechanism of action of some commonly used protein kinase inhibitors. *Biochem J*, 351, 95-105.

Grosse, R., Roelle, S., Herrlich, A., Hohn, J. and Gudermann, T. (2000) Epidermal growth factor receptor tyrosine kinase mediates Ras activation by gonadotropin-releasing hormone. *J Biol Chem*, 275, 12251-12260.

Kim, K. Y., Choi, K. C., Park, S. H., Auersperg, N. and Leung, P. C. (2004a) Extracellular signal-regulated protein kinase, but not c-Jun N-terminal kinase, is activated by type II gonadotropin-releasing hormone involved in the inhibition of ovarian cancer cell proliferation. *J Clin Endocrinol Metab*.

Kim, K. Y., Choi, K. C., Park, S. H., Chou, C. S., Auersperg, N. and Leung, P. C. (2004b) Type II gonadotropin-releasing hormone stimulates p38 mitogen-activated protein kinase and apoptosis in ovarian cancer cells. *J Clin Endocrinol Metab*, 89, 3020-3026.

Kimura, A., Ohmichi, M., Kurachi, H., Ikegami, H., Hayakawa, J., Tasaka, K., Kanda, Y., Nishio, Y., Jikihara, H., Matsuura, N. and Murata, Y. (1999) Role of mitogen-activated protein kinase/extracellular signal-regulated kinase cascade in gonadotropin-releasing hormone-induced growth inhibition of a human ovarian cancer cell line. *Cancer Res*, 59, 5133-5142.

Kraus, S., Levy, G., Hanoch, T., Naor, Z. and Seger, R. (2004) Gonadotropin-releasing hormone induces apoptosis of prostate cancer cells: role of c-Jun NH2-terminal kinase, protein kinase B, and extracellular signal-regulated kinase pathways. *Cancer Res*, 64, 5736-5744.

Miles, L. E., Hanyaloglu, A. C., Dromey, J. R., Pfleger, K. D. and Eidne, K. A. (2004) Gonadotropin-releasing hormone receptor-mediated growth suppression of immortalized LbetaT2 gonadotrope and stable HEK293 cell lines. *Endocrinology*, 145, 194-204.

Naor, Z., Harris, D. and Shacham, S. (1998) Mechanism of GnRH receptor signaling: combinatorial cross-talk of Ca2+ and protein kinase C. *Front Neuroendocrinol*, 19, 1-19.

Tanaka, Y., Gavrielides, M. V., Mitsuuchi, Y., Fujii, T. and Kazanietz, M. G. (2003) Protein kinase C promotes apoptosis in LNCaP prostate cancer cells through activation of p38 MAPK and inhibition of the Akt survival pathway. *J Biol Chem*, 278, 33753-33762.

Momany, F. A. (1976) Conformational energy analysis of the molecule, luteinizing hormone releasing hormone. I. Native decapeptide. *J Am Chem Soc*, 98, 2990-2996.

Enomoto, M., Endo, D., Kawashima, S, and Park, M. K. (2004) Human type II GnRH receptor mediates effects of GnRH on cell proliferation. Zoolog Sci, 21, 763-770.

Grundker, C., Gunthert, A. R., Westphalen, S. and Emons, G. (2002) Biology of the gonadotropin-releasing hormone system in gynecological cancers. *Eur J Endocrinol*, 146, 1-14.

Grundker, C., Schlotawa, L., Viereck, V., Eicke, N., Horst, A., Kairies, B. and Emons, G. (2004) Antiproliferative effects of the GnRH antagonist cetrorelix and of GnRH-II on human endometrial and ovarian cancer cells are not mediated through the GnRH type I receptor. *Eur J Endocrinol*, 151, 141-149.

Kaiser, U. B., Conn, P. M. and Chin, W. W. (1997) Studies of gonadotropin-releasing hormone (GnRH) action using GnRH receptor-expressing pituitary cell lines. *Endocr Rev*, 18, 46-70.

Limonta, P., Moretti, R. M., Marelli, M. M. and Motta, M. (2003) The biology of gonadotropin hormone-releasing hormone: role in the control of tumor growth and progression in humans. *Front Neuroendocrinol*, 24, 279-295.

Millar, R. P., Lu, Z. L., Pawson, A. J., Flanagan, C. A., Morgan, K. and Maudsley, S. R. (2004) Gonadotropin-releasing hormone receptors. *Endocr Rev*, 25, 235-275.

Morgan, K., Conklin, D., Pawson, A. J., Sellar, R., Ott, T. R. and Millar, R. P. (2003) A transcriptionally active human type II gonadotropin-releasing hormone receptor gene homolog overlaps two genes in the antisense orientation on chromosome 1q.12. Endocrinology, 144, 423-436.

Neill, J. D., Musgrove, L. C. and Duck, L. W. (2004) Newly recognized GnRH receptors: function and relative role. *Trends Endocrinol Metab*, 15, 383-392.

Song, P., Wei, J. and Wang, H. C. (2005) Distinct roles of the ERK pathway in modulating apoptosis of Ras-transformed and non-transformed cells induced by anticancer agent FR901228. *FEBS Lett*, 579, 90-94.

Davidson, L., Pawson, A. J., L Gópez de Maturana, R., Freestone, S. H., Barran, P., Millar, R. P. and Maudsley, S. (2004) Gonadotropin-releasing hormone-induced activation of diacylglycerol kinase-zeta and its association with active c-src. *J Biol Chem*, 279, 11906-11916.

Dikic, I. and Blaukat, A. (1999) Protein tyrosine kinase-mediated pathways in G protein coupled receptor signaling. *Cell Biochem Biophys*, 30, 369-387.

Farshori, P. Q., Shah, B. H., Arora, K. K., Martinez-Fuentes, A. and Catt, K. J. (2003) Activation and nuclear translocation of PKCdelta, Pyk2 and ERK1/2 by gonadotropin releasing hormone in HEK293 cells. *J Steroid Biochem Mol Biol*, 85, 337-347.

Grosse, R., Roelle, S., Herrlich, A., Hohn, J. and Gudermann, T. (2000) Epidermal growth factor receptor tyrosine kinase mediates Ras activation by gonadotropin-releasing hormone. *J Biol Chem*, 275, 12251-12260.

Kimura, A., Ohmichi, M., Kurachi, H., Ikegami, H., Hayakawa, J., Tasaka, K., Kanda, Y., Nishio, Y., Jikihara, H., Matsuura, N. and Murata, Y. (1999) Role of mitogen-activated protein kinase/extracellular signal-regulated kinase cascade in gonadotropin-releasing hormone-induced growth inhibition of a human ovarian cancer cell line. *Cancer Res*, 59, 5133-5142.

Kraus, S., Benard, O., Naor, Z. and Seger, R. (2003) c-Src is activated by the epidermal growth factor receptor in a pathway that mediates JNK and ERK activation by gonadotropinreleasing hormone in COS7 cells. *J. Biol Chem*, 278, 32618-32630.

Kraus, S., Levy, G., Hanoch, T., Naor, Z. and Seger, R. (2004) Gonadotropin-releasing hormone induces apoptosis of prostate cancer cells: role of c-Jun NH2-terminal kinase, protein kinase B, and extracellular signal-regulated kinase pathways. *Cancer Res*, 64, 5736-5744.

Limonta, P., Moretti, R. M., Marelli, M. M. and Motta, M. (2003) The biology of gonadotropin hormone-releasing hormone: role in the control of tumor growth and progression in humans. *Front Neuroendocrinol*, 24, 279-295.

Luttrell, L. M. (2003) 'Location, location, location': activation and targeting of MAP kinases by G protein-coupled receptors. *J Mol Endocrinol*, 30, 117-126.

Maudsley, S., Davidson, L., Pawson, A. J., Chan, R., Lopez de Maturana, R. and Millar, R. P. (2004) Gonadotropin-releasing hormone (GnRH) antagonists promote proapoptotic signaling in peripheral reproductive tumor cells by activating a Galphai-coupling state of the type I GnRH receptor. *Cancer Res*, 64, 7533-7544.

The invention claimed is:

1. A method of treating a reproductive cancer comprising administering to a subject a pharmaceutical composition comprising an agent comprising a peptide sequence selected from the group consisting of:

i) pLGlu-LHis-LTrp-LSer-LHis-DArg-LTrp-LTyr-LPro-A;

ii) pLGlu-LHis-LTrp-LSer-LHis-DTrp-LTrp-LTyr-LPro-A;

iii) pLGlu-LHis-LTrp-LSer-LTyr-DLys-LTrp-LGln-LPro-A;

iv) pLGlu-LHis-LTrp-LSer-LTyr-DLys-LTrp-LLeu-LPro-A;

v) pLGlu-LHis-LTrp-LSer-LTyr-DLys-LTrp-LTyr-LPro-A;

v-B) pLGlu-LHis-LTrp-LSer-LTyr-DLys-LTrp-LArg-LPro-A;

-continued vi) pLGlu-LHis-LTrp-LSer-LTyr-DTrp-LTrp-LArg-LPro-A;

vii) pLGlu-LHis-LTrp-LSer-LHis-DLys-LTrp-LTyr-LPro-A;

viii) pLGlu-LHis-LTrp-LSer-LHis-DArg-LTrp-LTyr-LPro.Y;

ix) pLGlu-LHis-LTrp-LSer-LHis-DArg-LLeu-LArg-LPro-A;

x) pLGlu-LHis-LTrp-LSer-LHis-DTrp-LTrp-LArg-LPro-A;

xi) pLGlu-LHis-LTrp-LSer-LHis-DTrp-LLeu-LArg-LPro-A;

xii) pLGlu-LHis-LTrp-LSer-LHis-DTyr-LLeu-LArg-LPro-A;

xiii) pLGlu-LHis-LTrp-LSer-LHis-DAla-LTrp-LTyr-LPro-A;

xiv) pLGlu-LHis-LTrp-LSer-LHis-DSer-LTrp-LTyr-LPro-A wherein
R2 is any D-amino acid except DTrp;
Y selected from the group consisting of NHEt, NH$_2$, DAla-NH$_2$, and Z; and
A is selected from the group consisting of:
Z;
azaL-Gly;
azaL-Gly-Z;
D-Ala-Z;
L-Glu-Z;
D-Ala-L-Glu-Z;
D-Ala-D-Ala-Z;
βAla-Z;
L-Pro;
L-Pro-Z;
D-Ala-L-Gly-Z; and
L-Gly-Z;
wherein Z is selected from the group consisting of NH$_2$, N-ethylamide (NHEt), N-propylamide, N-methylamide, and N-butylamide; and
a pharmaceutically acceptable carrier;
in an amount sufficient to treat the reproductive cancer in the subject.

2. The method of claim 1, wherein the reproductive cancer is selected from the group consisting of: gynecological cancer, prostate cancer, benign prostatic hyperplasia, endometrial cancer, cervical cancer, ovarian cancer, breast cancer, melanoma, pancreatic cancer, and gastric cancer.

3. The method of claim 1, wherein the subject is an animal.

4. The method of claim 3, wherein the animal is selected from the group consisting of: human, chicken, cat, dog, pig, sheep, cow, and horse.

5. A method for reducing proliferation of one or more reproductive cancer cells comprising combining with the one or more reproductive cancer cells a therapeutically effective amount of an agent comprising a peptide sequence selected from the group consisting of:

i) pLGlu-LHis-LTrp-LSer-LHis-DArg-LTrp-LTyr-LPro-A;

ii) pLGlu-LHis-LTrp-LSer-LHis-DTrp-LTrp-LTyr-LPro-A;

iii) pLGlu-LHis-LTrp-LSer-LTyr-DLys-LTrp-LGln-LPro-A;

iv) pLGlu-LHis-LTrp-LSer-LTyr-DLys-LTrp-LLeu-LPro-A;

v) pLGlu-LHis-LTrp-LSer-LTyr-DLys-LTrp-LTyr-LPro-A;

v-B) pLGlu-LHis-LTrp-LSer-LTyr-DLys-LTrp-LArg-LPro-A;

vi) pLGlu-LHis-LTrp-LSer-LTyr-DTrp-LTrp-LArg-LPro-A;

vii) pLGlu-LHis-LTrp-LSer-LHis-DLys-LTrp-LTyr-LPro-A;

viii) pLGlu-LHis-LTrp-LSer-LHis-DArg-LTrp-LTyr-LPro.Y;

ix) pLGlu-LHis-LTrp-LSer-LHis-DArg-LLeu-LArg-LPro-A;

x) pLGlu-LHis-LTrp-LSer-LHis-DTrp-LTrp-LArg-LPro-A;

xi) pLGlu-LHis-LTrp-LSer-LHis-DTrp-LLeu-LArg-LPro-A;

xii) pLGlu-LHis-LTrp-LSer-LHis-DTyr-LLeu-LArg-LPro-A;

xiii) pLGlu-LHis-LTrp-LSer-LHis-DAla-LTrp-LTyr-LPro-A;

xiv) pLGlu-LHis-LTrp-LSer-LHis-DSer-LTrp-LTyr-LPro-A wherein
R2 is any D-amino acid except DTrp;
Y selected from the group consisting of NHEt, NH$_2$, DAla-NH$_2$, and Z; and
A is selected from the group consisting of:
Z;
azaL-Gly;
azaL-Gly-Z;
D-Ala-Z;
L-Glu-Z;
D-Ala-L-Glu-Z;
D-Ala-D-Ala-Z;
βAla-Z;
L-Pro;
L-Pro-Z;
D-Ala-L-Gly-Z; and
L-Gly-Z;

wherein Z is selected from the group consisting of $NH_2$, NHEt, N-propylamide, N-methylamide, and N-butylamide.

6. The method according to claim 5, wherein the one or more reproductive cancer cells are from a reproductive cancer selected from the group consisting of: gynecological cancer, prostate cancer, benign prostatic hyperplasia, endometrial cancer, cervical cancer, ovarian cancer, breast cancer, melanoma, pancreatic cancer, and gastric cancer.

7. The method according to claim 5, wherein the one or more reproductive cancer cells are from an animal's body.

\* \* \* \* \*